(12) United States Patent
Nuttall

(10) Patent No.: US 7,279,276 B2
(45) Date of Patent: Oct. 9, 2007

(54) SCREENING METHOD

(75) Inventor: Patricia Anne Nuttall, Culham (GB)

(73) Assignee: Evolutec Limited, Reading, Berkshire (GB)

( * ) Notice: Subject to any disclaimer, the term of this patent is extended or adjusted under 35 U.S.C. 154(b) by 217 days.

(21) Appl. No.: 10/178,912

(22) Filed: Jun. 24, 2002

(65) Prior Publication Data

US 2003/0008333 A1    Jan. 9, 2003

Related U.S. Application Data

(63) Continuation of application No. PCT/GB00/05001, filed on Dec. 22, 2000.

(30) Foreign Application Priority Data

Dec. 23, 1999   (GB) .................... 9930564.1

(51) Int. Cl.
*C12Q 1/68* (2006.01)
(52) U.S. Cl. ............................... 435/6; 435/7.1
(58) Field of Classification Search ............. 435/6, 435/701
See application file for complete search history.

(56) References Cited

FOREIGN PATENT DOCUMENTS

| | | | |
|---|---|---|---|
| EP | 0 404 055 A1 | * | 5/1990 |
| EP | 0404055 A1 | | 12/1990 |
| EP | 0404055 B1 | | 12/1990 |

OTHER PUBLICATIONS

Wang et al. Immunglobulin G binding proteins in the ixodid ticks, *Rhipicephalus appendiculatus, Amblyomma variegatum* and *Ixodes hexagonus* Parsitology (1995), 111, 161-165.*
Titus et al., FASEB Journal, 13:A954 (1999).
Wang et al., Parasitology, 111:161-165 (1995).
Wang et al., Parasitology, 109:525-530 (1994).

* cited by examiner

*Primary Examiner*—James Ketter
(74) *Attorney, Agent, or Firm*—Klauber & Jackson

(57) ABSTRACT

The invention relates to methods for the identification of novel receptors and/or novel ligands. The invention is based on the concept that parasites have developed a number of biologically active compounds in their saliva to cope with the defense mechanisms of the host organisms on which they feed and to manipulate the biological functions of host molecules to their advantage. These saliva compounds can be used to identify novel molecules within the host systems. Furthermore, these saliva compounds can be used to elucidate the functions of molecules whose existence is already known.

14 Claims, 19 Drawing Sheets

A  SDS-PAGE under reducing condition

B  SDS-PAGE under non-reducing condition

1 - NC
2 - fMLP
3 - IL-8
4 - anti-IL8
5 - SGE
6 - fr.35
7 - fr.39
8 - fr. 50-52

Anti-chemokine activity of FPLC fractions (400 μl) of SGE derived from 11-12 days fed *Amblyomma variegatum* male ticks (65 ticks, 2,39 mg proteins) - ELISA A) 100 pg IL-8    (15 μl)
B) 120 pg MIP-1a  (2,5 μl)
C)  80 pg MCP-1   (5 μl)
D)  60 pg RANTES  (10 μl)

Anti-chemokine activity of FPLC fractions (400 µl) of SGE derived from 5 days fed *Rhipicephalus appendiculatus* female ticks (121 ticks, 1.966 mg proteins) - ELISA A) 100 pg IL-8 (5 µl)

B) 125 pg MIP-1α (7.5 µl)

SCREENING METHOD

This is a request for filing a continuation application under 37 CFR 1.53(b) of pending prior international application Number PCT GB00/05001, filed on Dec. 22, 2000 entitled SCREENING FOR HOST-MOLECULES INTERACTING WITH PARASITE-SGE-RELATED COMPOUNDS which designated the United States.

This invention relates to methods for the identification of novel receptors and/or novel ligands. The invention is based on the concept that parasites have developed a number of biologically-active compounds in their saliva to cope with the defence mechanisms of the host organisms on which they feed and to manipulate the biological functions of host molecules to their advantage. These saliva compounds can be used to identify novel molecules within the host systems. Furthermore, these saliva compounds can be used to elucidate the functions of molecules whose existence is already known.

In nature, all water-soluble signalling molecules, such as neurotransmitters, protein and peptide hormones and growth factors, act through receptors. These receptors may be soluble or may be cell surface-bound. They bind reversibly to their ligand and in this fashion act to convert extracellular ligand binding events into one or more intracellular signals that alter the behaviour of target cells.

There are a large number of biological ligands known, and in most cases, the receptors that bind these ligands are also known. However, the inventors consider it likely that a large number of bioactive ligands and receptors remain unidentified at present. Indeed, large scale sequencing projects such as the Human Genome Project are generating large amounts of sequence data at a hitherto unparalleled speed. Despite recent improvements in the field of bioinformatics, there is a significant lag between obtaining results from sophisticated sequence generating techniques and the development of effective methods that are capable of accurately predicting the functions of the proteins that are encoded by these genes. Furthermore, for those prediction programs that do exist, it is likely that many proteins that possess functions as bioactive ligands and receptors are not identified using these techniques. Accordingly, there remains a great need for the development of methods that are effective to identify novel ligands and receptors and to elucidate the functions of these molecules.

According to the present invention, there is provided a method for identifying a receptor or ligand with a biological function in a host organism, said method comprising the steps of:
a) bringing a sample of biological material from a host organism that is suspected of containing the receptor or ligand into contact with a compound derived from the saliva or salivary glands of a blood-feeding parasite; and
b) isolating from the sample, one or more receptors or ligands that bind to the parasite salivary compound.

Nature has designed numerous compounds that can complete a necessary task with great precision—to control blood flow, to prevent pain and itching, to stop inflammation, to regulate immune responses and even to glue human skin. The inventors consider one of the most prolific sources of such evolutionary compounds to be the salivary glands of blood-feeding parasites.

When parasites feed on blood they expose themselves to the formidable defensive armoury of their hosts whose complexity of chemical cascades and cellular responses has evolved to ward them off. Even histamine, one of the pharmacological triggers for the inflammatory response, is thought to have arisen as a protective mediator against endoparasites and ectoparasites.

The survival of leeches, mosquitoes, ticks and all other blood-sucking parasites has depended on the evolution of sophisticated countermeasures. Their strategy is to produce pharmacologically-active protective molecules in their salivary glands. These saliva molecules are injected into their host when they feed. Some parasites, including most insects that feed on blood, (for example mosquitoes and horse flies) feed rapidly. The pharmacopoeia in their saliva provides for a hit-and-run approach. For example, they produce highly potent vasodilators and anticoagulants that maximise the amount of blood available in a short time.

The greatest challenge among blood-sucking parasites is that faced by ticks. These relatives of spiders and scorpions attach to their hosts, penetrate the skin, insert their mouthparts (often cementing them in place) and then feed for anything up to two weeks. Often their hosts feel nothing. In contrast, the lesser trauma that is caused by a thorn in the flesh is immediately painful and rapidly becomes swollen.

Ticks are allowed to feed undisturbed because they have developed a series of pharmacologically-active compounds in their saliva. These molecules are injected into the skin of the host where they control natural defence mechanisms such as blood clotting, inflammation and immune responses. Because ticks have needed to do this to survive for hundreds of millions of years, the compounds have been finely tuned by evolution to be highly efficient in their function and to exhibit low toxicity in their hosts.

The saliva of ticks is believed to contain a plethora of molecules, each tailored to a specific function or to more than one function, such as to eliminate histamine, to prevent blood coagulation, to control complement and even to stabilise mast cells. Secretion of each group of molecules is switched on or off by the tick as blood-feeding progresses. Unsurprisingly, the salivary glands of ticks are large and complex.

The blood-feeding strategies of insects and ticks are highly successful. Indeed, probably no other foreign proteins have been regularly injected into mammals over such a vast period of time. Thus, it is highly likely that the "defence molecules" present in tick saliva have evolved to have a high margin of safety and low immunogenicity for the host species whilst retaining their potent pharmacological effects.

The present invention is based upon the realisation, hitherto unrecognised, that the saliva of blood-feeding parasites can be exploited to identify novel receptors and receptor ligands and to elucidate the biological functions of putative receptors and receptor ligands in host species. The underlying concept embodied in this invention is that through their evolution over millions of years, parasites have developed a huge pharmacopoeia of compounds in their saliva, all of which must have a biologically-relevant function. If each molecule did not have a function that was biologically important, its existence in saliva would have no purpose. Its production by the parasite would therefore waste energy and resources, the scarcity of which makes survival a finely-balanced matter in any event. Evolutionary theory would dictate that over the course of time, more efficient parasite organisms would have survived in preference to those organisms that wasted energy or resources by producing unnecessary saliva proteins.

For example, a cytokine regulator produced by blood-feeding ticks has been found to interact with the receptor of the cytokine (Hajnická et al., (2000) Inhibition of the Antiviral Action of Interferon by Tick Salivary Gland Extract; Parasite Immunology 22: 201-206). This prevents the binding of the cytokine to its receptor and thereby inhibits the host reactions that result from the binding of the cytokine with its receptor. A different cytokine regulator produced by blood-feeding ticks has also been identified that interacts directly with the cytokine itself, rather than with the cytokine receptor, and that thereby inhibits the activity of the cytokine (see co-pending, co-owned United Kingdom patent application GB0003245.8).

By "receptor" is meant any macromolecule that functions to bind a ligand in a host organism. The receptor may be either a membrane-bound receptor, such as an extracellular or intracellular membrane-bound protein receptor, or may be a soluble receptor.

By "receptor ligand" is meant a ligand that interacts in a host organism with a receptor as this term is defined above. Examples of such ligands include hormones, neurotransmitters, drugs, vasoactive amines (such as histamine and serotonin), cytokines and intracellular messengers. Although many of the molecules that function as biological ligands and messengers are now known, the inventors consider it likely that a significant number of equivalent ligand or receptor molecules remain to be identified, certainly in mammalian host organisms.

By "biological function" is meant that the receptor or ligand has some bioactive function in the host organism. Such bioactive functions include metabolic functions in regulating the level of a particular metabolite or group of metabolites, binding functions in titrating the amount of a compound in a biological fluid such as blood, messenger functions, functions as mediators of inflammatory processes and recruiters of defence mechanisms, immunomodulators such as cytokines, functions in dilating or contracting blood vessels, modulators of antibody-related and other immune responses and so on. Other biological functions will be clear to those of skill in the art.

Obvious examples of host organisms that are suitable for analysis according to the method of the present invention include mammals, birds, fish and reptiles. It is likely that mammals, particularly domesticated and companion animals, and humans will be the host organisms whose systems will be of the greatest interest.

The method of the invention allows the identification and isolation of host molecules by virtue of their binding affinity for molecules that are present in parasite saliva. Accordingly, in order to isolate such host molecules successfully, a process must be used that separates those molecules that exhibit specific affinity for parasite compounds from those that do not. The parasite compound may be free in solution, affixed to a solid support, borne on a cell surface or located intracellularly. Particularly suitable methods include methods of affinity separation, for example, using columns or other supports on which parasite or host compounds have been immobilised (see, for example, Wang, H. and Nuttall, P. A. (1994), Parasitology 109: 525-530). Suitable supports include any suitably inert material such as gels, magnetic and other beads, microspheres, binding columns and resins. When a sample of biological material from a host or parasite organism is passed over the support, those molecules exhibiting affinity for their binding partners will bind to the support and will be retained when non-binding compounds are washed off.

Other examples include antigen panning; methods that utilise plasmon resonance detection (such as BIACORE™) (Karlsson et al., (2000) Anal Biochem 278(1), 1-13); competitive binding assays; the yeast two hybrid system; the use of nuclear magnetic resonance and labelled proteins (for example, using $C^{13}$, or $N^{15}$) to screen mixed libraries (Hadjuk et al., (1999) J Med Chem 42(13), 2315-7; Moore J M (1999) Curr. Opin. Biotechnol. 10, 54-8); the confocor (Nicoli et al., (1980) Proc. Natl. Acad. Sci. USA, 77: 4904-4908); and methods based on the detection of enzymatic activities (for example, Cox et al., (2000) Prog Med Chem 37, 83-133; Freeman (2000) Med Res Rev 20(3), 197-202; Sundberg (2000) Curr Opin Biotechnol 11(1), 47-53; White (2000) Annu Rev Pharmacol Toxicol 40, 133-57).

Methods for the immobilisation of host or parasite compounds onto a support will be clear to those of skill in the art, and include covalent attachment by chemical means through modification of the compounds to include reactive groups (see, for example, "Protein purification, a Practical Approach", IRL Press) and less disruptive means that utilise non-covalent attachment mechanisms such as chelating compounds, tags, and antibodies.

Parasite salivary compounds may be used in a number of different ways to isolate ligands or receptor compounds from a host organism. In its simplest embodiment, the invention will use a single type of parasite compound as a capture substrate, immobilised onto a solid support. Such a compound may, for example, be a protein, peptide or a small non-peptidic molecule derived from the saliva or salivary glands of a blood-feeding parasite. Peptides and proteins may be either recombinantly-produced or purified in their native form. Furthermore, included as compounds "derived" from parasite saliva or salivary glands are synthetic molecules such as synthetic peptides, that correspond in sequence to peptides present in parasite saliva and bioactive fragments and truncated forms of parasite saliva proteins.

Alternatively, more than one parasite compound type may be used as the capture reagent. In one embodiment, a preparation of parasite saliva may be used, that contains a plethora of different compounds, each with its own target or targets in the host organism. Salivary gland extracts may also be used, or fractions of parasite salivary extracts.

In a preferred embodiment, a parasite salivary gland expression library may be used. Such a library contains all of the peptides and proteins that are expressed in the saliva of the parasite and will thus allow separation from the host organism of all the compounds that exhibit affinity for any one of these parasite peptides and proteins. A partial expression library may also be used.

In a further embodiment, the genes encoding parasite proteins may be cloned into an expression library in such a way that a library of fusion proteins is produced. Such a method may be used, for example, to facilitate the immobilisation of parasite proteins onto a support. Suitable fusion systems include the glutathione S transferase and polyhistidine tag systems. Other examples will be clear to the skilled reader. For example, metal chelating peptides such as histidine-tryptophan modules allow purification on immobilised metals, protein A domains allow purification on immobilised immunoglobulin, and the domain utilised in the FLAGS extension/affinity purification system (Immunex Corp., Seattle, Wash.) may also be used. A useful discussion of vectors that contain fusion proteins is provided in Kroll, D. J. et al., 1993 (DNA Cell Biol. 12:441-453).

In certain scenarios, such as when performing an initial large scale screen, it may be desired to use more than one parasite species in order to maximise the opportunity of identifying biologically-relevant compounds present in the host organism. For example, salivary preparations or expression libraries from a selection of different tick species might be used in such a screen.

The identification of compounds from the host organism may also be achieved using a number of alternative strategies. In a simplest embodiment, a biological fluid, such as blood, lymph or cerebrospinal fluid, may be used in a method of affinity purification, by passing the fluid, or an extract of the fluid, over a support onto which compounds from parasite saliva have been immobilised. Of course, as discussed above, it may in some circumstances be found more preferable for the host proteins to be immobilised onto the support as capture reagents and for a preparation of parasite saliva to be passed over this support. Bound parasite compounds may then by isolated for further analysis.

Rather than using a fluid such as blood, it may be found preferable to use a number of different host protein types or one single protein type to identify compounds that bind to compounds in parasite saliva. Such host proteins may be isolated in their native form or may alternatively be produced recombinantly. For example, an expression library from the host organism, or from a particular cell type in the host organism, may be used to identify binding partners in parasite saliva. In such an expression library, each host protein will be cloned under the control of a heterologous promoter system, normally in a prokaryotic host. Suitable expression systems are known to those of skill in the art (see, for example, Sambrook J., Fritsch E. F. and Maniatis T. (1989) Molecular Cloning: A Laboratory Manual. Cold Spring Harbour Laboratory; Protein Expression in Current Protocols in Molecular Biology (Chapter 16). Editors: F. M. Ausubel, R. Brent, R. E. Kingson, D. D. Moore, J. G. Seidman, J. A. Smith, K. Struhl. Published by John Wiley and Sons, Inc.)

It is envisaged that this embodiment of the invention holds great promise for the identification of biologically-active compounds that are present in host organisms. For example, as the human genome sequencing project generates more and more data, it is becoming clear that there are a large number of orphan receptors to which no function has yet been assigned. The methods of the present invention allow the identification of ligands for such molecules by identifying equivalent molecules that are present in parasite saliva. This will facilitate the elucidation of the function of these orphan receptors and the generation of drug molecules directed against these receptors that are likely to possess useful properties in therapy and diagnosis of human and animal disease.

In a further aspect of the invention, polyclonal antisera or monoclonal antibodies produced against parasite proteins can be used to immunoprecipitate either the native (for example, if using saliva or salivary gland extracts) or recombinant parasite protein after the parasite protein has been introduced to host tissue or derivatives. It can be expected that in vivo, the parasite proteins will form complexes with their host protein binding partners, and the complexes will co-precipitate. The precipitates resulting from such work can then be analysed (for example, by SDS-PAGE, perhaps combined with a gel-overlay method such as that described by Otto (1986, Methods Enzymol. 134, 555-560) or a modified farwestern technique (Lieberman and Berk (1991, Genes Dev. 5, 2441-2454)) to identify the interacting host protein. Alternatively, the host protein can be partially or completely sequenced. Partial protein sequences will allow the construction of primers, which can then be used in PCR-reactions to amplify host genomic DNA or to screen cDNA-libraries, for further characterisation of the protein and the encoding genes.

If polyclonal antibodies are desired, a selected mammal, such as a mouse, rabbit, goat or horse, may be immunised with a compound derived from saliva or salivary gland extract. The polypeptide used to immunise the animal can be derived by recombinant DNA technology or can be synthesized chemically. If desired, the polypeptide can be conjugated to a carrier protein, such as bovine serum albumin, thyroglobulin or keyhole limpet haemocyanin. The coupled polypeptide is then used to immunise the animal. Serum from the immunised animal is collected and treated according to known procedures, for example by immunoaffinity chromatography.

Monoclonal antibodies to the parasite compound may also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

In a further aspect of the invention, wound-site libraries can be constructed using mRNA from tissue on which blood-feeding parasites have fed, such as, for example, the skin of a mammal. Wound-site mRNA can be isolated from cells washed out of the bite-site after removal of the parasite, and homogenates of tissue lining the feeding lesions obtained from skin biopsies. Cells migrating out of skin explants (taken at the bite-site) into culture medium (which in mammalian hosts will be cell types such as Langerhans cells, monocytes, neutrophils, γδ-T cells and so on; Larsen et al., (1990), J. Exp. Med. 172, 1483-1493) can also be used as a source of mRNA.

Other library types may also be produced. For example, matchmaker cDNA-libraries (Clontech) can be used. This system is an eukaryotic in vivo genetic assay that makes it possible to screen rapidly a group of fusion proteins (for example, recombinant wound-site proteins) for interaction with a specific parasite protein, and immediately to identify the gene that codes for the interacting wound-site protein. If necessary, library construction can be adapted for use with secreted and membrane proteins, for example, by deliberately avoiding transcription into full-length clones by using "short copy" reverse transcription, so that signal sequences are at least partially deleted.

Lambda "wound-site" expression libraries can also be developed. Plaque lifts can be screened with labelled parasite proteins. Alternatively, they can be localised by binding of tagged conjugates (for example, using nickel-nitrilotriacetic-acid-alkaline phosphatase conjugates (Qiagen) and histidine-tags (Botting and Randall (1995), BioTechniques 19, 362-363)).

Phage display libraries would allow the biopanning of recombinant parasite proteins, to screen for interacting host proteins (for example, using a phage-display wound-site library). Alternatively, a eukaryotic display library system can be used (for example, an insect cell library), based on the expression of foreign cDNAs on the surface of a virus such as a baculovirus (see, for example, Davies (1995) Bio/Technology 13, 1046; Boublik et al., (1995) Bio/Technology 13, 1079-1084).

The strategies discussed above involving expression libraries allow for the characterisation and identification of the interacting wound-site protein(s) by sequencing the corresponding wound site cDNAs.

Interactions between parasite salivary gland proteins and wound-site proteins can also be investigated in a general way, starting from a pool of parasite salivary gland proteins and a pool of host wound-site proteins. Parasite-host protein hybrids can be obtained and the corresponding host cDNA molecule sequenced. In one sense, phage-display technology can be used. The objective in this instance is to obtain phage-display libraries representing parasite salivary gland mRNA, as well as phage-display libraries constructed with mRNA taken from cells from the feeding site on the host, and to look for interactions between 'salivary-gland phages' and 'wound-site phages'.

A phagemid vector system such as that described by Otto (1986) is well-suited for this approach, although other systems will be readily apparent to the skilled reader. In this example, foreign proteins are fused to the C-terminus of the minor coat protein VI, resulting in a functional and accessible recombinant protein, even if the foreign cDNAs code for hydrophobic signal sequences. Prior to the fusion of foreign cDNAs to the gene encoding protein VI, the vector can be modified by introducing specific epitopes at the N-terminus of protein III; different epitopes (against which commercial antisera are available) are used to mark the wound-site libraries and the parasite salivary gland libraries. Antisera can thus be used to distinguish the libraries at all times, to immobilise selectively either the wound-site or the salivary-gland library, and to extract interacting phages, which will be bound by both antisera and that can thus be isolated using two consecutive affinity column purifications. Selectively immobilising one of the 2 libraries may be necessary to minimise undesired interactions, for example, interactions between nuclear proteins. By immobilising a fraction of the salivary-gland library and pre-incubating this fraction with an excess of salivary-gland phages, most binding sites for nuclear factors (and other, undesired proteins) will already be occupied, before wound-site phages are allowed to interact.

In certain embodiments of the invention, competitive binding assays may be used to assess or to analyse binding affinity exhibited between parasite and host compounds. For example, a parasite salivary compound can be used in a competitive screening assay to characterise a receptor or receptor ligand. Such an assay would include a compound derived from the saliva or salivary glands of a parasite, together with a host receptor and a number of ligands. As the skilled reader will appreciate, one or more of the ligand, receptor and parasite compounds may be uncharacterised. Other components, such as labels and detection means, will also form part of such a system. Suitable assays will be known to those of skill in the art and include assays such as ELISA.

Host molecules that are identified by virtue of their affinity for a parasite salivary compound will preferably be isolated for further analysis. Non-proteinaceous compounds, such as small non-peptidic ligands, can be purified and analysed to examine their composition and structure. Proteinaceous compounds may also be purified from the support by conventional means and sequenced at their N termini. These sequences may be used to develop probes suitable for the identification of the coding gene in the host organism.

Various methods now exist that allow the concomitant selection with an isolated compound of the gene that encoded it. For example, International patent application WO99/02671 describes a method whereby the gene that encodes a displayed protein is compartmentalised within a microcapsule and is thus linked to its product. In the present invention, this would be advantageous since, upon isolation of a protein that binds to a compound in parasite saliva, its encoding gene would be isolated at the same time. Other methods of linking genotype to phenotype will be known to those of skill in the art.

In a further aspect of the invention there is provided a method of screening for a gene encoding a receptor or encoding a receptor ligand with a biological function in a host organism, comprising the steps of:
a) bringing a nucleic acid molecule derived from said host organism that is suspected of containing the receptor or ligand into contact with a nucleic acid molecule encoding a molecule present in the saliva or salivary glands of a blood-feeding parasite, under conditions suitable for the hybridisation of homologous nucleic acid molecules; and
b) isolating from the sample, host-derived nucleic acid molecules that hybridise with said parasite nucleic acid molecules.

In this embodiment of the invention, a preparation of nucleic acid from a parasite is compared with a preparation of nucleic acid from a host organism for that parasite. The theory underlying this aspect of the invention is that parasite and host nucleic acid molecules that share sequence homology may be inferred to possess a common function. For example, a peptide found in the saliva or salivary glands of a parasite species, that is highly homologous with a peptide or fragment of a protein from a host species, may be inferred to have evolved to mimic the function of the host protein in some way. This makes it possible in one sense to elucidate the function of the host peptide or protein. It also allows for the use of the parasite peptide in a host organism to manipulate the biological process in which this host protein or peptide is involved. It also allows the development of compounds, such as small molecule antagonists, that mimic the effect of the parasite peptide.

In this aspect of the invention, both the host-derived and parasite-derived nucleic acid molecules are generally oligonucleotides of at least 15 nucleotides in length, preferably at least 30 nucleotides in length, more preferably 50 nucleotides or longer. The greater the length of oligonucleotide used, the more the possibility is reduced that hybridisation occurs between nucleic acid molecules that are not complementary. Standard non-stringent conditions are generally used for the hybridisation of nucleic acid molecules (6×SSC/50% formamide at room temperature, or equivalent conditions) and washed under conditions of low stringency (2×SSC, room temperature, 2×SSC, 42° C., or equivalent conditions). More usually, conditions of higher stringency will be used (such as 0.1×SSC, 65° C., or equivalent conditions) (where SSC=0.15M NaCl, 0.015M sodium citrate, pH 7.2).

The nucleic acid molecules used in the method of this aspect of the invention may be single- or double-stranded DNA, cDNA or RNA. Preferably, the nucleic acid molecules comprise single-stranded DNA.

In a preferred embodiment of this aspect of the invention, the screening method may be carried out using gene array technology. Nucleic acid arrays considerably facilitate the large scale screening of nucleic acid molecules at a low cost. Detailed information regarding the design and construction of arrays may be found in the literature, particularly in the following documents: U.S. Pat. No. 5,925,525; US 5,922, 591, WO99/35256; WO99109218; WO98/56954; U.S. Pat. No. 5,837,832 and US 5,770,722.

These methods, based on techniques pioneered by Schena et al., 1995 (Science 270: 467-470) and Fodor et al., 1991 (Science 251, 767-773) also facilitate the evaluation of variations in the nucleic acid sequence of DNA or RNA samples and so allow the identification and genotyping of mutations and polymorphisms in these sequences. It is thus hypothesised that these techniques may be used in the system of the present invention to identify mutations and polymorphisms that are implicated in various disease states in the host organism. For example, parasite nucleic acids, or nucleic acid molecules developed from parasite sequences that encode molecules with affinity for a host receptor protein implicated in susceptibility to conditions such as asthma, conjunctivitis or allergic rhinitis might be used to screen host individuals for variations in these genes. Recent advances in this technology include those reported by Brown and Botstein (1999, Nature Genet. 21:25-32); Hacia (1999, Nature Genet. 21, 42-27) and Wang et al., (1998, Science 280:1077-1082) and reviewed generally in Nature Genetics 21, supplement 1 (January 1999). Gene chips are likely to be particularly useful in this embodiment of the invention.

Parasites suitable for analysis according to the present invention include any blood-feeding parasite. The parasite may be an ectoparasite or an endoparasite. Preferably, the parasite is an ectoparasite such as a tick, a mosquito, a horsefly or other blood-sucking insect, or a leech or other blood-sucking worm. Particularly suitable tick species include Ixodid ticks such as *Rhipicephalus appendiculatus*, *Dermacentor reticulatus*, *Amblyomma variegatum*, *Ixodes ricinus* and *Ixodes hexagonus*, and argasid ticks such as *Ornithodoros moubata*.

According to a further aspect of the invention, there is provided a host receptor, ligand or gene identified by any one of the screening methods described above. The invention also provides such a host receptor, receptor ligand or gene, for use as a pharmaceutical. In a still further aspect, there is provided the use of a bioactive parasite salivary compound in a screening assay to characterise the function of a host receptor, ligand or gene.

EXAMPLES

Materials and Methods

Preparation of Tick Salivary Gland Extract (SGE)

*Dermacentor reticulatus* and *Ixodes ricinus* ticks were collected by flagging the vegetation in selected localities of western Slovakia. All other tick species examined were obtained from laboratory colonies (Jones et al, 1988). Adult ticks were allowed to feed on Balb-C or ICR female mice, or guinea pigs, or rabbits, as described previously (Jones et al, 1988; Kubes et al, 1994). After the specified number of days of feeding, female ticks were gently removed from the animals and their salivary glands dissected out on ice, washed with saline, and homogenised in pools of salivary glands in a final volume of 10 μl per tick. The protein concentration of the clarified supernatant was determined using the Bradford method (Bradford, 1976). Samples were dried using a Speed-Vac, stored at 4° C., and rehydrated prior to use.

Fractionation of Tick SGE by Fast Phase Liquid Chromatography (FPLC)

Figure 1:
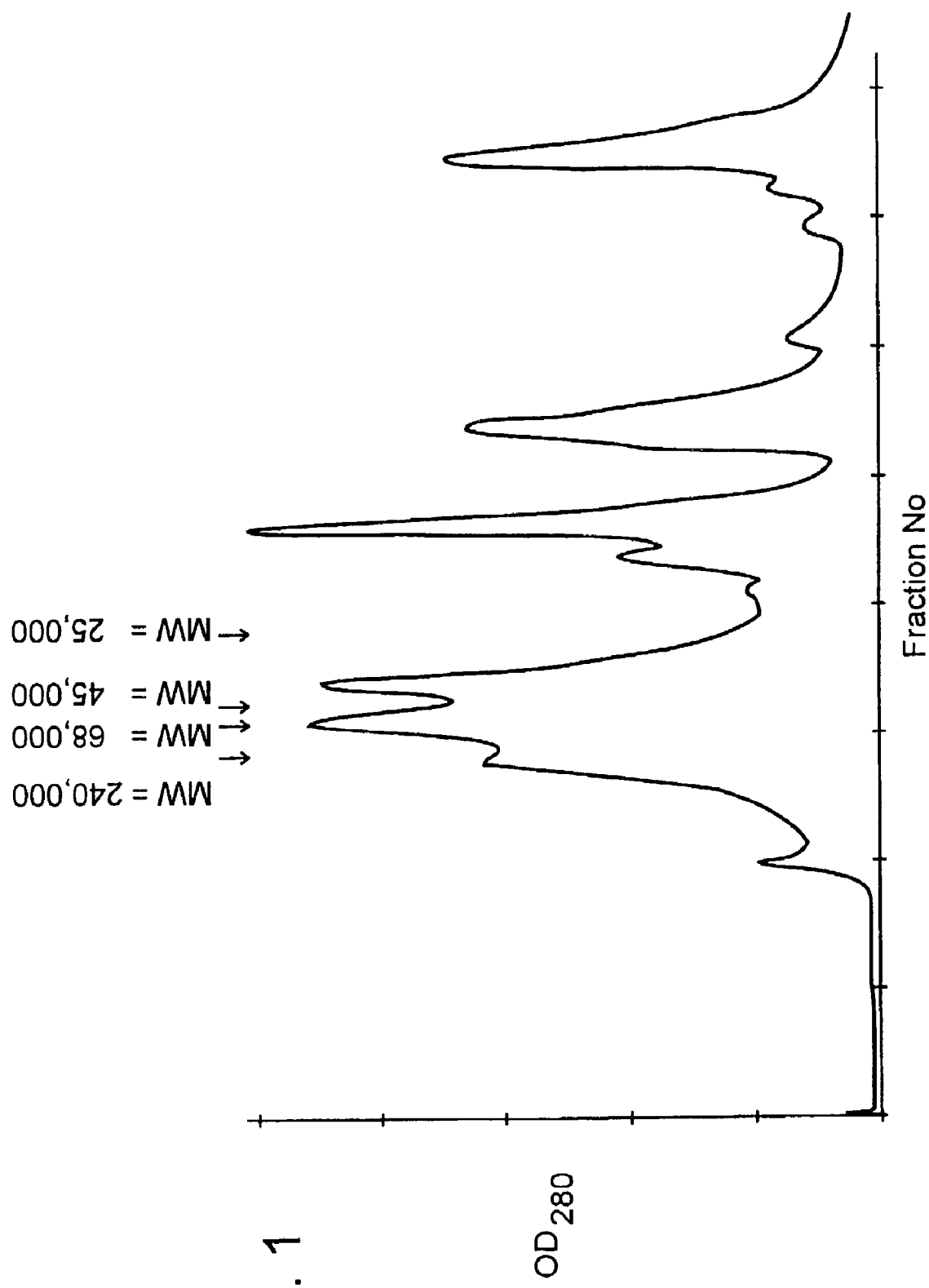
FIG. 1 shows the fractionation of salivary gland extract (SGE) of *Dermacentor reticulatus* adult female ticks fed for 5 days using fast phase liquid chromatography (FPLC). Arrows indicate the positions of molecular weight markers (Boehringer).

Pooled SGE preparations that had been dried using a Speed-Vac and stored in eppendorf tubes in 1200 to 5000 μg amounts were solubilised by adding to each eppendorf sample 30 μl 0.02 M Tris HCl pH 7.5. After being held for 60 min at 5° C., the suspension was centrifuged 10 min × 15,000 g. The sediments were re-extracted 3 times and then all four preparations were pooled and then centrifuged 10 min at 15,000 g. The supernatant (100 μl) was separated by liquid chromatography under native conditions at 5° C. using a Superose 12 HR 10/30 column (Pharmacia) with an equilibrium buffer of 0.02 M Tris HCl, 0.15 M NaCl, pH 7.5, and a sample volume of 100 μl, flow rate of 0.4 ml/min and one fraction collected per min. An example of the separation of SGE derived from *D. reticulatus* adult females fed for 5 days is shown in FIG. 1.

Detection of IL-8 by Enzyme-linked Immunoabsorbent Assay (ELISA)

The IL-8/Nap-1 ELISA Bender MedSystems kit (Cat. No. BMS204MS) was used, with recombinant human interleukin-8 (72 amino acids) from Research Diagnostics Inc., USA (Cat. No. RDI-208M). The IL-8 was prepared by dissolving 25 μg (1 ampoule) in 1 ml 0.1% bovine serum albumin. Five μl aliquots were stored at −70° C. (5 μl=125 ng IL-8). Before the test, IL-8 was diluted in Leibowitz medium supplemented with 5% of bovine serum and mixed for 2 hr at room temperature with the test sample (SGE or FPLC fractions of SGE) by gentle shaking. Aliquots of 50 μl containing a final concentration of about 100 pg of IL-8 and 5 μl of test sample per well were applied in duplicate to the ELISA plate. Washing and optical density measurements were carried out using a DYNATECH LABORATORIES apparatus.

Detection of Chemokines other than IL-8 by Enzyme-linked Immunoabsorbent Assay (ELISA).

Human chemokines were detected using specific ELISA kits according to the manufacture's instructions. Kits were from R&D Sytems (Quantikine® Assays), Abingdon, U.K. MIP-1α (Cat. No. DMA00), RANTES (Cat. No. DRN00), and MCP-1 (Cat. No. DCP00). For each assay, 110 μl chemokine were mixed with 10 μl of SGE or FPLC fractions of SGE in eppendorf tubes. Each mixture was incubated 2 hr at room temperature by gentle shaking. Duplicate 50 μl aliquots were applied to the ELISA plate. Washing and optical density (O.D.) measurements at 450 nm were carried out using a Dynatech Laboratories apparatus.

Sodium Dodecyl Sulphate—polyacrylamide Gel Electrophoresis (SDS-PAGE)

SDS-PAGE with discontinuous buffers was carried out in a gradient of 7.5 to 12.5% polyacrylamide in 1.5 mm thick gels (Laemmli, 1979) in reducing or non-reducing conditions (with or without β-mercaptoethanol, respectively).

Example 1

Effect of Tick SGE on the Detection of IL-8 Produced by the Human Monocytic Leukaemia Cell Line, THP-1

The human monocytic leukaemia cell line, THP-1, was obtained from the German Collection of Microorganisms and Cell Cultures, Germany. The cells were grown in RPMI-1640 medium supplemented with 10% foetal bovine serum, 100 U/ml penicillin, 100 μg/ml streptomycin, and 0.25 μg/ml amphotericin B at 37° C. in a humidified atmosphere containing 5% $CO_2$.

Figure 2:
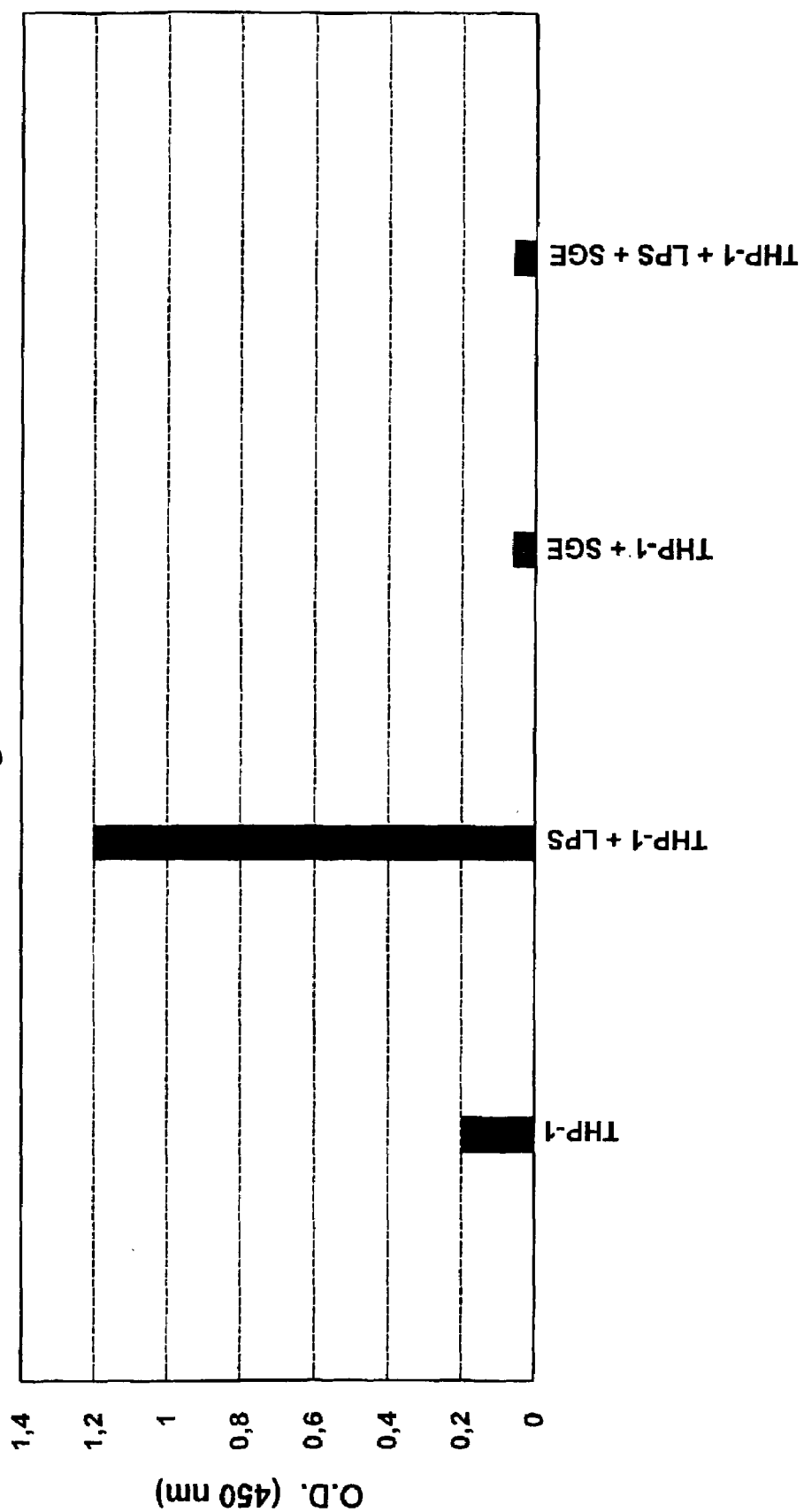
FIG. 2 shows the effect of tick SGE on IL-8 production by the human monocytic leukemic cell line, THP-1, measured by enzyme linked immunoabsorbent assay (ELISA). LPS=lipopolysaccharide; SGE from *D. reticulatus* adult females fed for 5 days.

When the cells were treated with lipopolysaccaride (LPS) from *E. coli* serotype 026:B6 (SIGMA-ALDRICH CHEMIE GmbH), a high level of IL-8 was detected by ELISA (FIG. 2). A low level of IL-8 was detected for cells not stimulated with LPS.

In the presence of SGE from *D. reticulatus* adult females fed for 5 days, using either LPS-stimulated or unstimulated (no LPS) THP-1 cells, the amount of IL-8 detected by ELISA was reduced to levels comparable to those of the control blank (0.06) indicating that no IL-8 was detectable.

This work shows that a compound(s) present in the salivary extract isolated from *D. reticulatus* ticks may be used to bind to and allow the extraction of the cytokine IL-8 from cell culture media.

Example 2

Comparison of Treatment with SGE Derived from Different Tick Species on the Detection of IL-8

100 pg human recombinant IL-8 were incubated for 2 hr with 5.5 μg SGE derived from various ixodid tick species (*D. reticulatus, A. variegatum, R. appendiculatus, Ixodes ricinus,* and *Haemaphysalis inermis*). The amount of IL-8 was then measured by ELISA.

Figure 3:
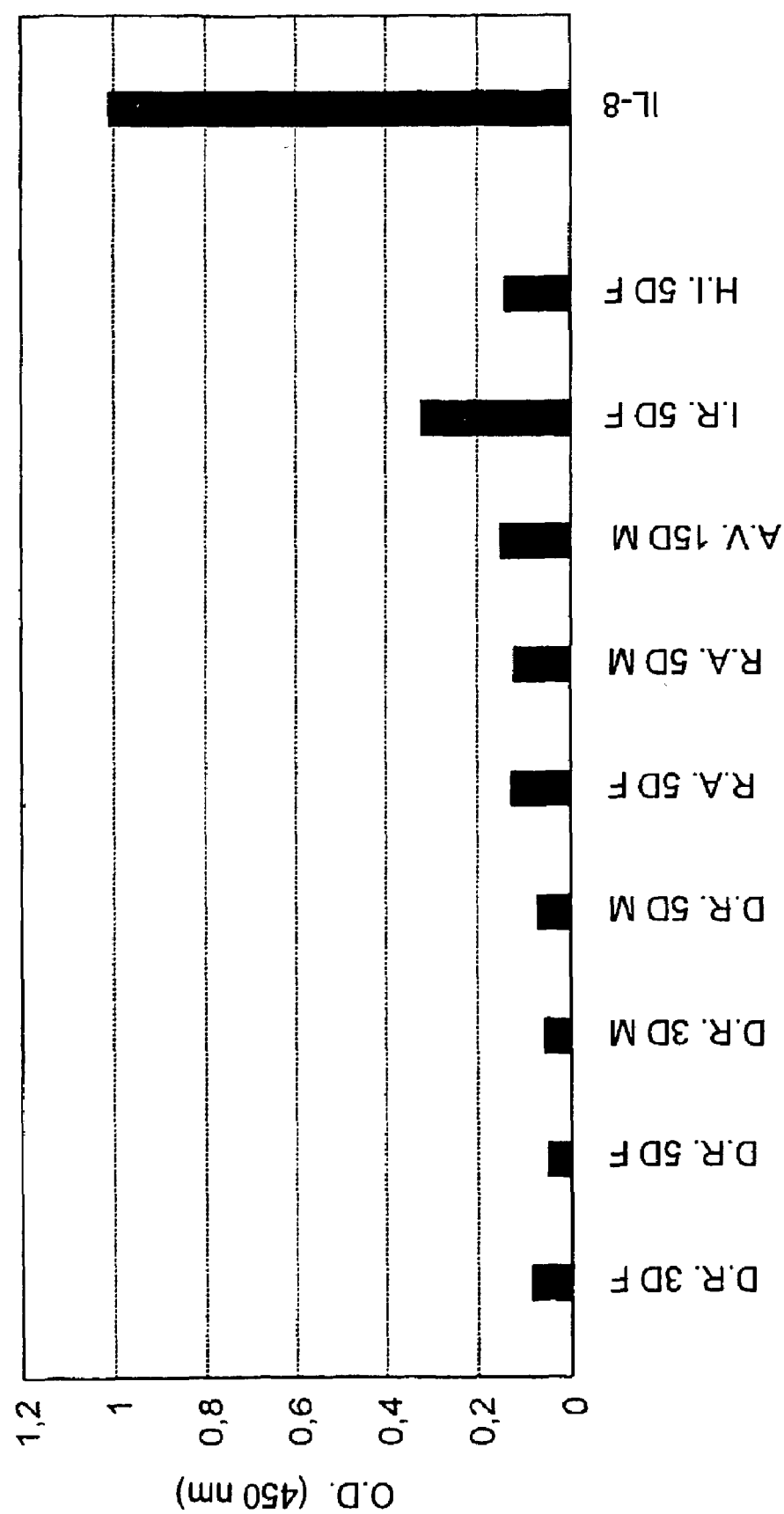
FIG. 3 shows the detection by ELISA of 100 pg of IL-8 after 2 hours incubation with SGE from different tick species. D.R. 3D F=*Dermacentor reticulatus* adult females fed for 3 days; D.R. 5D F=*D. reticulatus* adult females fed for 5 days; D.R. 3D M=*D. reticulatus* adult males fed for 3 days; D.R. 5D M=*D. reticulatus* adult males fed for 5 days; R.A. 5D F=*Rhipicephalus appendiculatus* adult females fed for 5 days; R.A. 5D M=*R. appendiculatus* adult males fed for 5 days; A.V. 15D M=*Amblyomma variegatum* adult males fed for 15 days; I.R. 5D F=*Ixodes ricinus* adult females fed for 5 days; H.I. 5D F=*Haemaphysalis inermis* adult females fed for 5 days; IL-8=IL-8 alone not treated with SGE.

FIG. 3 shows that the amount of detectable IL-8 was reduced significantly by treatment with tick SGE. The greatest reduction occurred with SGE from *D. reticulatus* adult females fed for 5 days.

This work shows that compounds present in the salivary extract isolated from five different tick species may be used to bind to and allow the extraction of the cytokine IL-8 from assay preparations containing IL-8.

Example 3

Effect of FPLC Fractions of *D. reticulatus* SGE on the Level of IL-8

100 pg human recombinant IL-8 were incubated for 2 hr with 10 µl FPLC fractions of *D. reticulatus* adult females (5.2 mg from 74 ticks) or males (3.3 mg from 293 ticks) fed for 5 days. The amount of IL-8 was then measured by ELISA.

Figure 4:
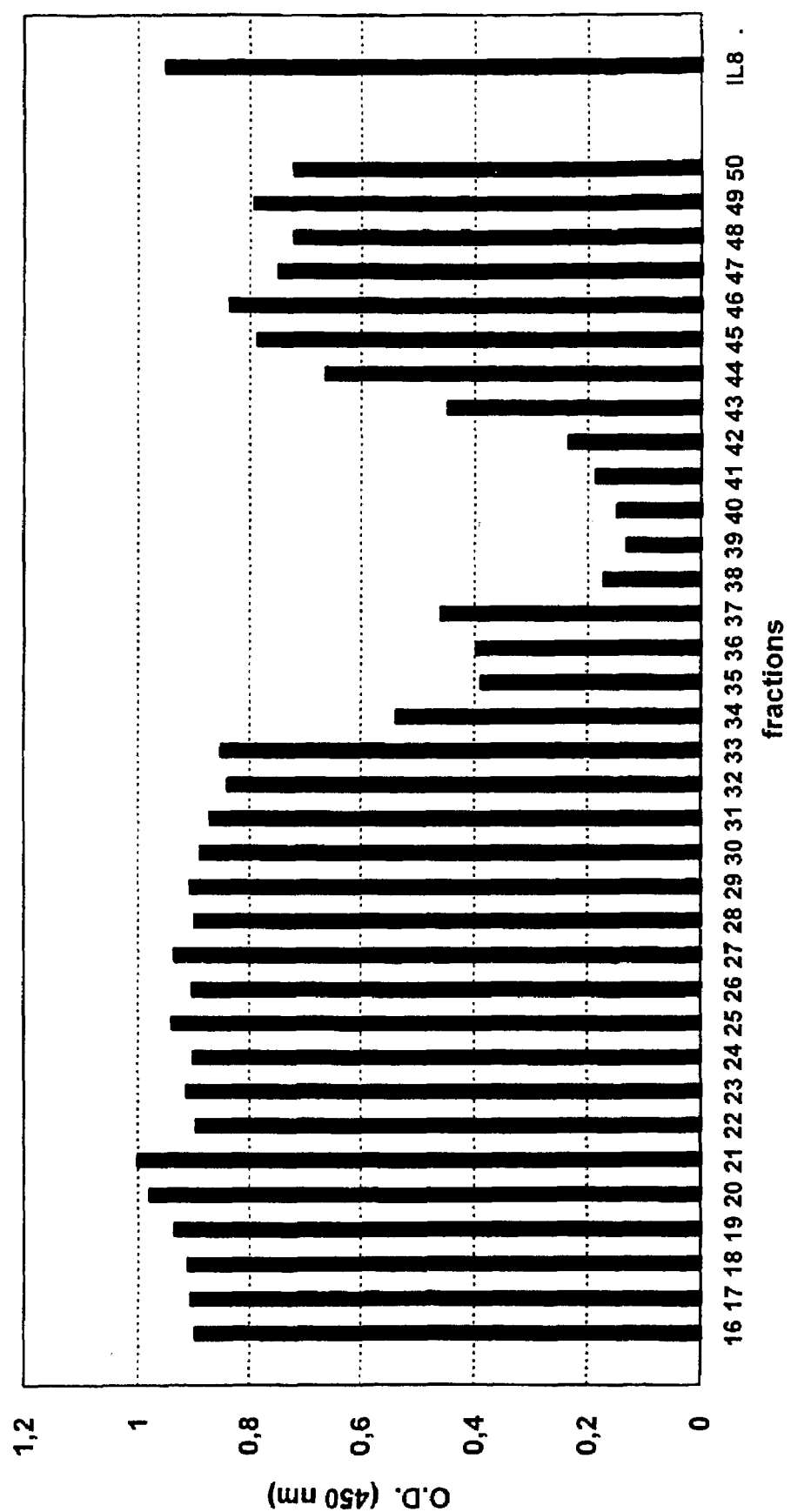
FIG. 4 shows the detection by ELISA of 100 pg of IL-8 after 2 hours incubation with FPLC fractions of SGE derived from *D. reticulatus* adult females fed for 5 days.
Figure 5:
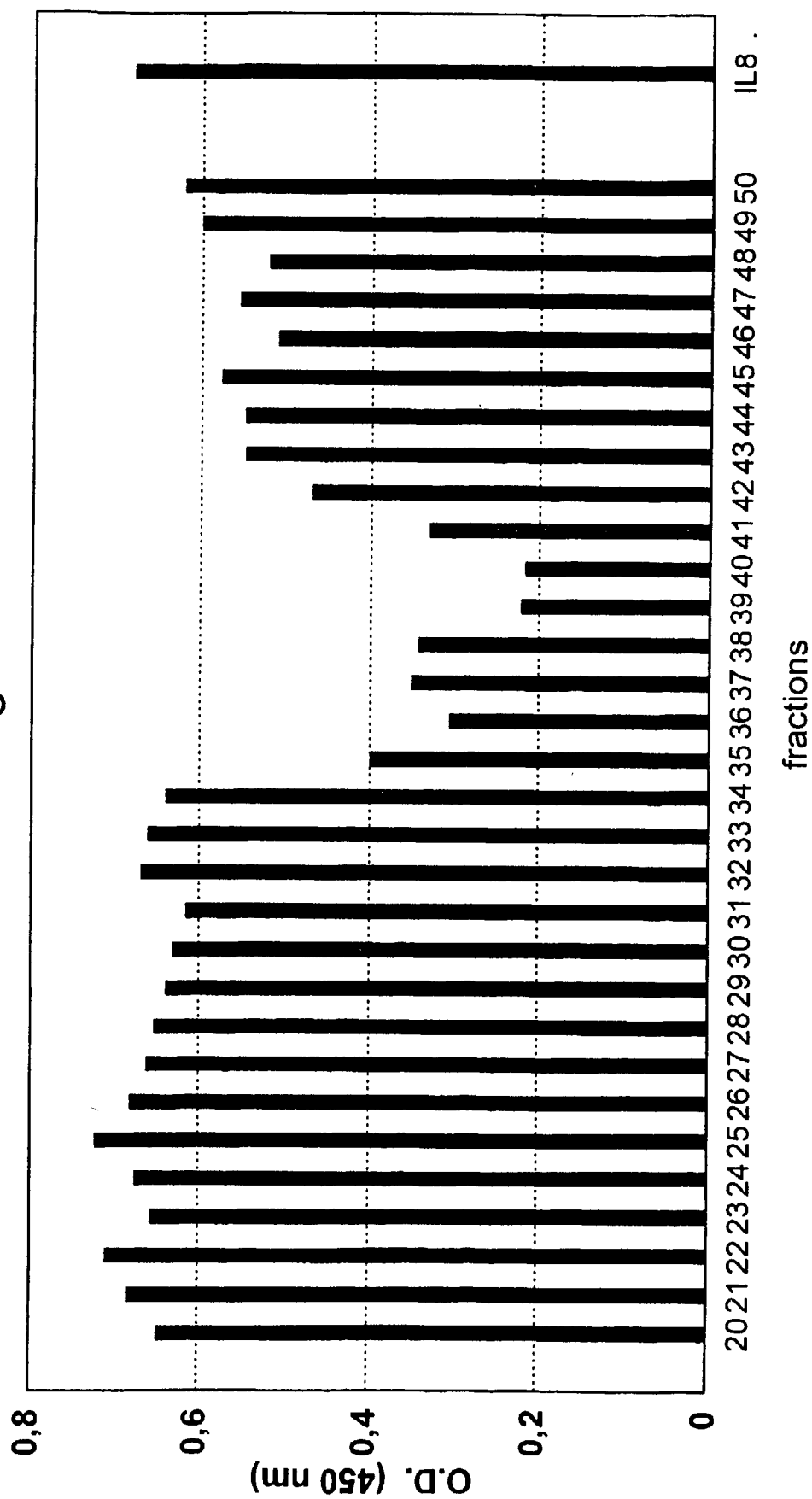
FIG. 5 shows the detection by ELISA of 100 pg of IL-8 after 2 hours incubation with FPLC fractions of SGE derived from *D. reticulatus* adult males fed for 5 to 6 days.

FIGS. 4 and 5 show that the fractionated SGE of female and male ticks, respectively, contains two peaks of anti-IL-8 activity. The greatest level of activity was in the peak including fractions 39 and 40 while a second less active peak included fraction 36.

These fractions may be used to bind to and allow the extraction of the cytokine IL-8 from assay preparations containing IL-8, so providing a method for fishing a ligand (such as IL-8) from mixed preparations containing the ligand. In an alternative method, these fractions may be used to raise antibodies against components of the SGE. By binding antibodies such as these to a solid support or matrix, and passing a solution of SGE+cytokine over the support or matrix, cytokine may be selectively isolated from the medium. By manipulating the physical conditions so as to cause dissociation of cytokine, this component may then be selectively separated.

Example 4

Effect of Protease Inhibitors of the Action of Tick SGE on IL-8

Tablets of an EDTA-free protease inhibitor cocktail (Boehringer Mannheim GmbH, Germany) were each dissolved in 2 ml water. The metalloproteinase inhibitor, ethylenediaminetetraacetic acid (EDTA) disodium salt (SIGMA) was used at a final concentration of 5 mM.

Ten µl SGE were mixed with 10 µl protease inhibitor. For the protease inhibitor cocktail, after 15 min incubation, IL-8 was added and after a further 2 hr incubation, the level of IL-8 was determined by ELISA. For EDTA treatment, SGE and the inhibitor were incubated for 1 hr before IL-8 was added for a further 1 hr prior to ELISA.

Figure 6:
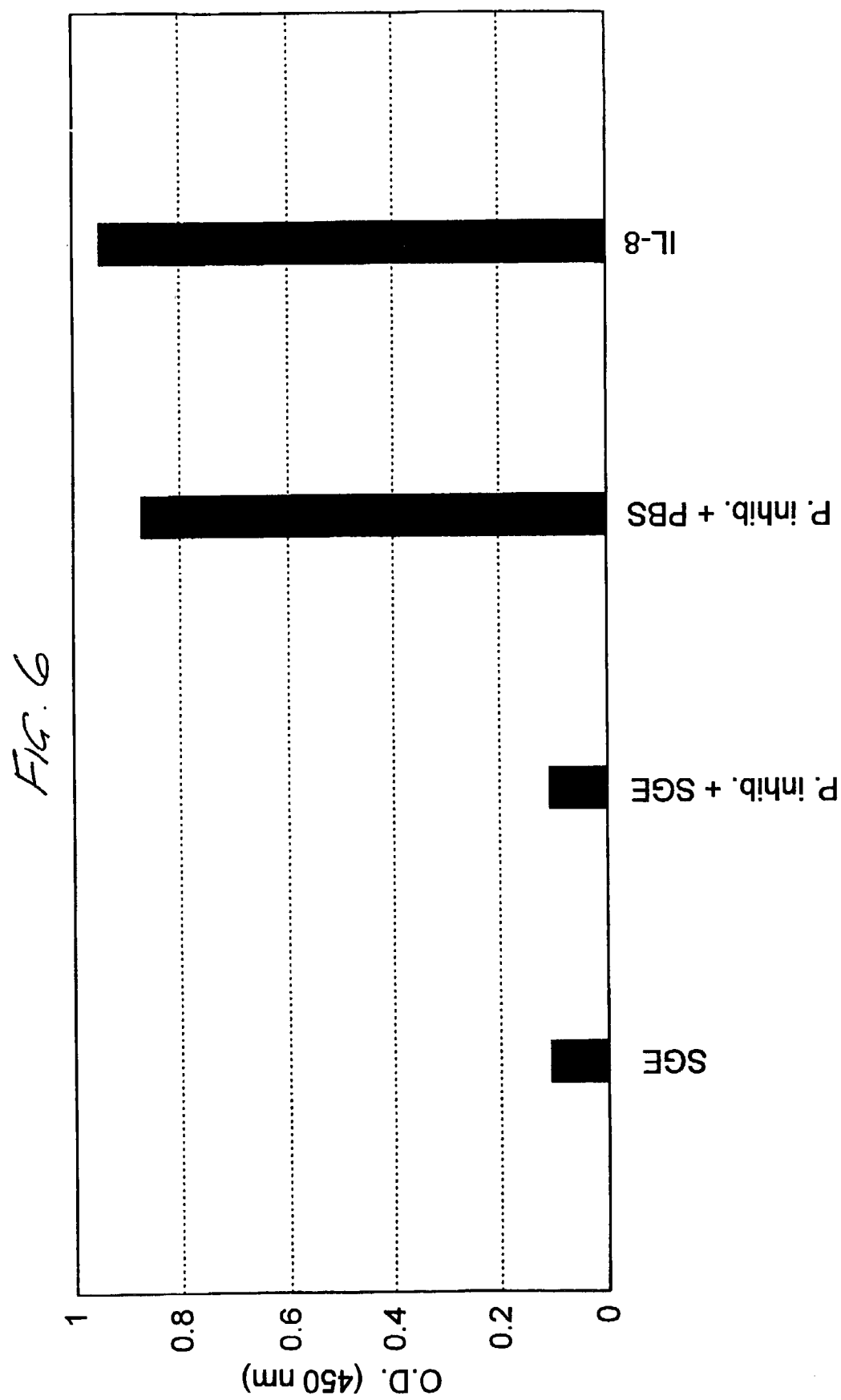
FIG. 6 shows the detection by ELISA of IL-8 after incubation with *D. reticulatus* SGE pretreated with a protease inhibitor cocktail. P. inhib.=protease inhibitor; PBS=phosphate buffered saline (control).

The protease inhibitor cocktail affected neither the amount of IL-8 in the absence of SGE (control) nor the decrease in IL-8+SGE, indicating that the anti-IL-8 effect of the SGE was not due to proteolytic activity (FIG. 6).

Figure 7:
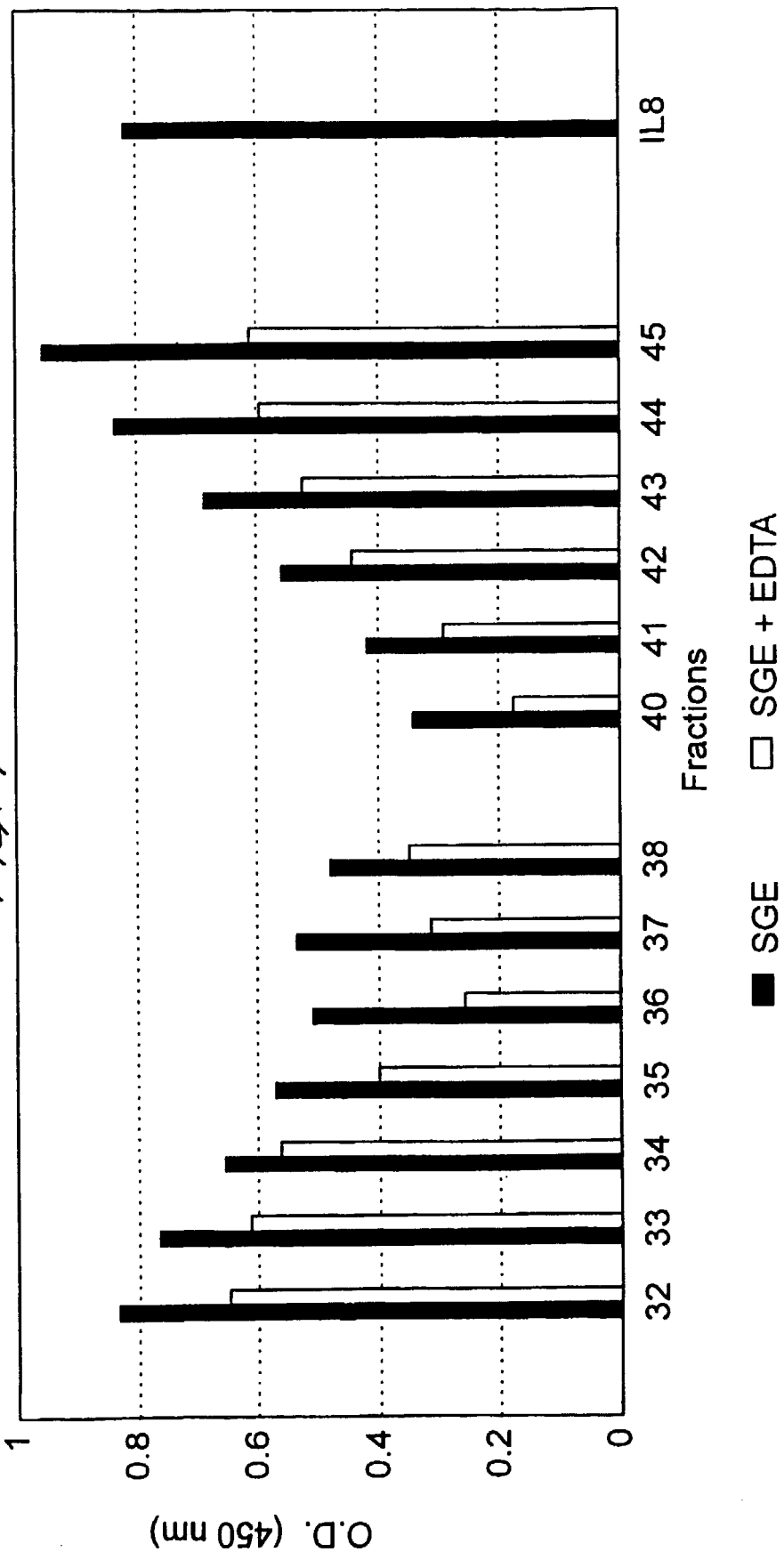
FIG. 7 shows the detection by ELISA of 100 pg of IL-8 after incubation with FPLC fractions of SGE derived from *D. reticulatus* adult females that were either untreated (SGE) or treated with the metalloproteinase inhibitor, ethylene diamine tetraacetic acid (SGE+EDTA).

FIG. 7 shows that anti-IL-8 activity remained following treatment with EDTA indicating that anti-IL-8 activity is not due to the action of a metalloproteinase in tick SGE.

Example 5

Binding of $I^{125}$-IL-8 to Tick SGE

Human recombinant $^{125}I$/-Interleukin-8 was obtained from NEN Life Science Products, USA (Cat. No. NEX277); Immobilon-P transfer PVDF membranes from MILLIPORE, USA (Cat. No. IPVH 304 F0); and goat anti-human IL-8 IgG from Research Diagnostics Inc., USA (Cat. No. RDI-IL8 abgx). One mg of the goat antibody was dissolved in 1 ml of sterile distilled water and stored in aliquots of 10 µl at −70° C.

Drops (5 to 10 µl) of samples (SGE, FPLC fractions of SGE, anti-IL-8 antibodies) were allowed to absorb 45 mins at 4° C. to pre-wetted membranes. Membranes were washed in 50 ml TTBS (20 mM Tris-HCl, 500 mM NaCl, 0.05% Tween-20, pH 7.5) for 10 min and unoccupied sites on the membranes were saturated with 15 mil TTBS+3% bovine serum albumin (BSA) for 1 hr at room temperature. Then membranes were washed in 40 ml of TTBS (for 10 mins plus two times for 5 mins) and incubated in 5 ml of TTBS pH 8+100 µl $^{125}$I-IL-8 for 90 mins at room temperature by gentle shaking. Finally, membranes were washed again in 30 ml TTBS (1× for 10 mins and 5× for 5 mins), dried and then exposed 3-4 days to X-ray film (CRONEX, DU PONT).

Figure 8:
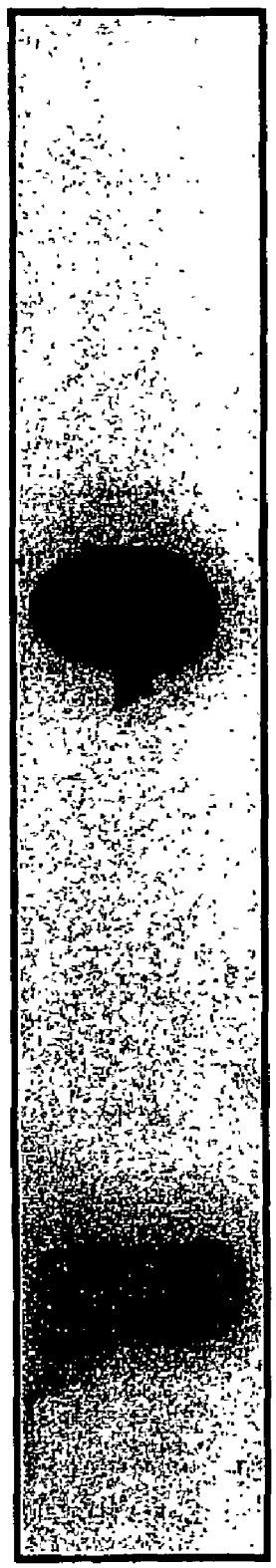
FIG. 8 shows the binding of $^{125}$I-IL-8 to SGE of *D. reticulatus* adult females fed for 5 days. A) shows the radiolabel bound to SGE and B) shows the radiolabel bound to anti-IL8 antibody (positive control).
Figure 9:
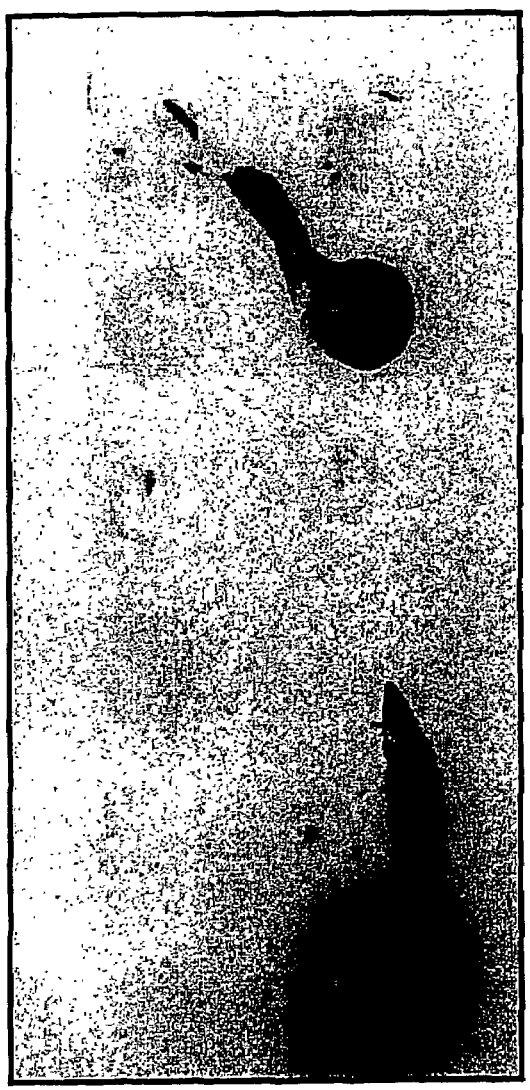
FIG. 9 shows the binding of $^{125}$I-IL-8 to selected FPLC fractions of SGE derived from different tick species. A=*D. reticulatus* adult females fed for 5 days, fraction 35; B=*D. reticulatus* adult females fed for 5 days, fraction 40; C=*R. appendiculatus* adult females fed for 5 days, fraction 39; E=*R. appendiculatus* adult females fed for 5 days, fraction 32; F=goat anti-IL-8 (positive control).
Figure 9:
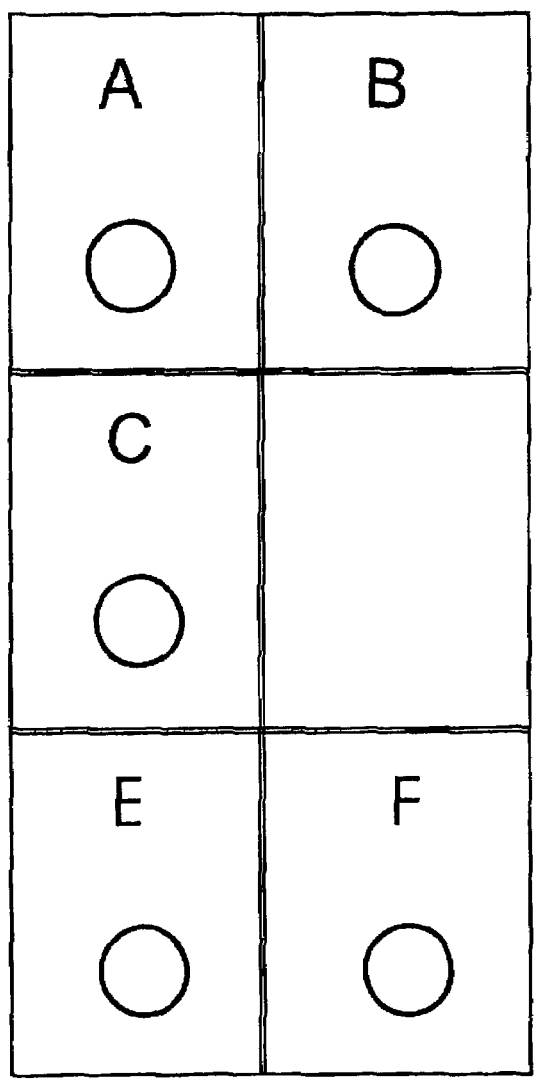
Figure 10:
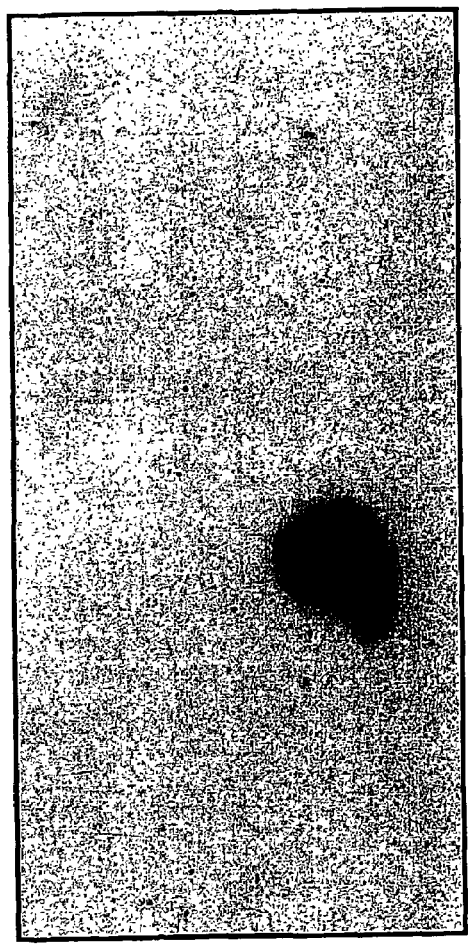
FIG. 10 shows the binding of $^{125}$I-IL-8 to selected FPLC fractions of SGE derived from *D. reticulatus* adult females. A=fraction 16; B=fraction 21; C=fraction 32; D=fraction 39; F=fraction 26.
Figure 10:
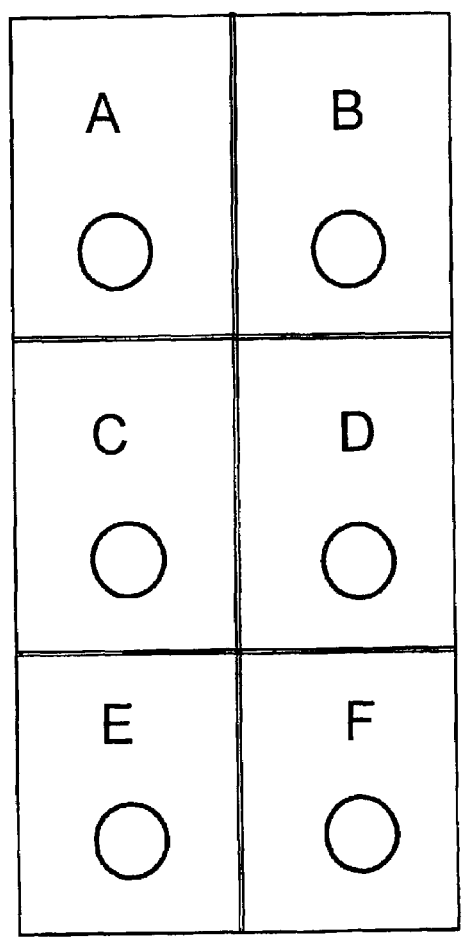

Samples were dot-blotted onto the membranes, in the volumes: FIG. 8: A, 5 µl; B, 10 µl; FIG. 9: A, B, C, E, F, 10 µl; FIG. 10: A, B, C, D, E, F, 5 µl.

In FIG. 8, the radiolabelling of SGE treated with $^{125}$I-IL-8 indicates that anti-IL-8 activity is due to a factor(s) in tick SGE that binds to IL-8.

The results shown in FIG. 9 indicate that FPLC fraction 40 of SGE from *D. reticulatus* adult females fed for 5 days has very strong IL-8 binding activity and that weak binding activity is shown by the other fractions tested.

FIG. 10 results indicate that FPLC fraction 39 has very strong IL-8 binding activity, whereas fraction 32 has very weak binding activity and the other fractions tested did not bind to IL-8.

Example 6

Cross-linking of $I^{125}$-IL-8 to Tick SGE

Sodium dodecyl sulphate—polyacrylamide gel electrophoresis (SDS-PAGE) with discontinuous buffers was carried out in a gradient of 7.5 to 12.5% polyacrylamide in 1.5 mm thick gels (Laemmli, 1979) in reducing or non-reducing conditions (with or without β-mercaptoethanol, respectively).

FPLC fractions of SGE were dialysed in PBS for 1 hr. Two µl of $^{125}$I-IL8 were added to 30 µl of either the FPLC fraction or PBS. Then, 1.6 µl of either the stock solution of crosslinker, dithiobis sulfosuccinimidylpropionate (DTSS) from Pierce (1.7 mg of DTSSP dissolved in 0.139 ml PBS at a 20 mM concentration) prepared just prior to use, or PBS were added to the samples. Final concentration of DTSSP was 1 mM in the reaction mixture. Samples were incubated for 30 mins at room temperature. The crosslinking reaction was quenched for 15 mins by adding 1.1 µl of TRIS solution pH 7.5 at a final concentration of 30 mM in the reaction mixture.

Crosslinked products were observed (FIG. 11) with a band in fraction 35 running at approximately 30 to 40 kD and a band in fraction 41 of approximately 14 to 20 kD.

Figure 11:
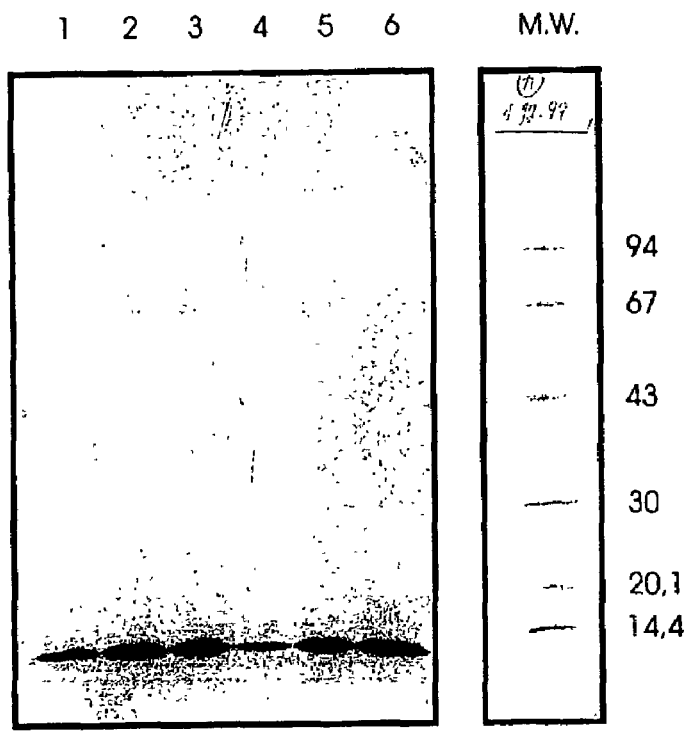
FIG. 11 shows cross-linking of $^{125}$I-IL-8 to selected FPLC fractions of SGE derived from *D. reticulatus* adult females fed for 5 days. Sodium dodecyl sulphate—polyacrylamide gel electrophoresis (SDS-PAGE) run under either reducing (A) conditions with β-mercaptoethanol, or non-reducing (B) conditions i.e. without β-mercaptoethanol. Samples in lanes 1 to 3 were not cross-linked whereas samples in lanes 4 to 6 were cross-linked with DTSSP. Lane 1=$^{125}$I-IL-8; lane 2=$^{125}$I-IL-8+fraction 35; lane 3=$^{125}$I-IL-8+fraction 41; lane 4=$^{125}$I-IL-8; lane 5=$^{125}$I-IL-8+fraction 35; lane 6=$^{125}$I-IL-8+fraction 41; M.W.=molecular weight markers.
Figure 11:
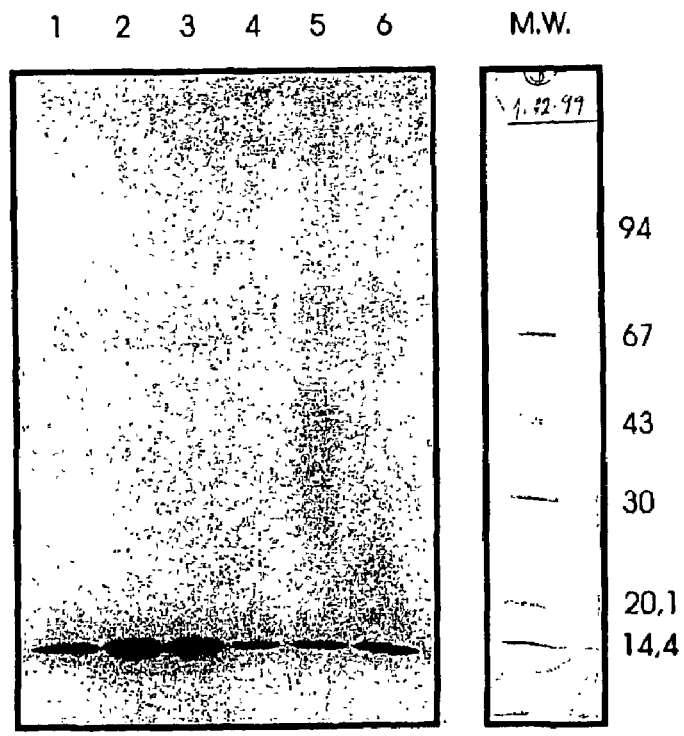

The results shown in FIG. 11 confirm that a molecule(s) in SGE binds to IL-8. The results also confirm that it is possible to cross-link SGE components with bioactive compounds from tissue culture media, so facilitating their separation and isolation for further study.

Example 7

Binding of $I^{125}$-IL-8 to FPLC Fraction 40 of *D. reticulatus*

Fraction 40 was resolved by SDS-PAGE gel electrophoresis. The gel was electroblotted onto PVDF membranes in Towbin transfer buffer (25 mM Tris, 192 MM glycine, 20% methanol, pH 8.3) at 30 V and 100 mA for 16 hr at 10° C.

Figure 12:
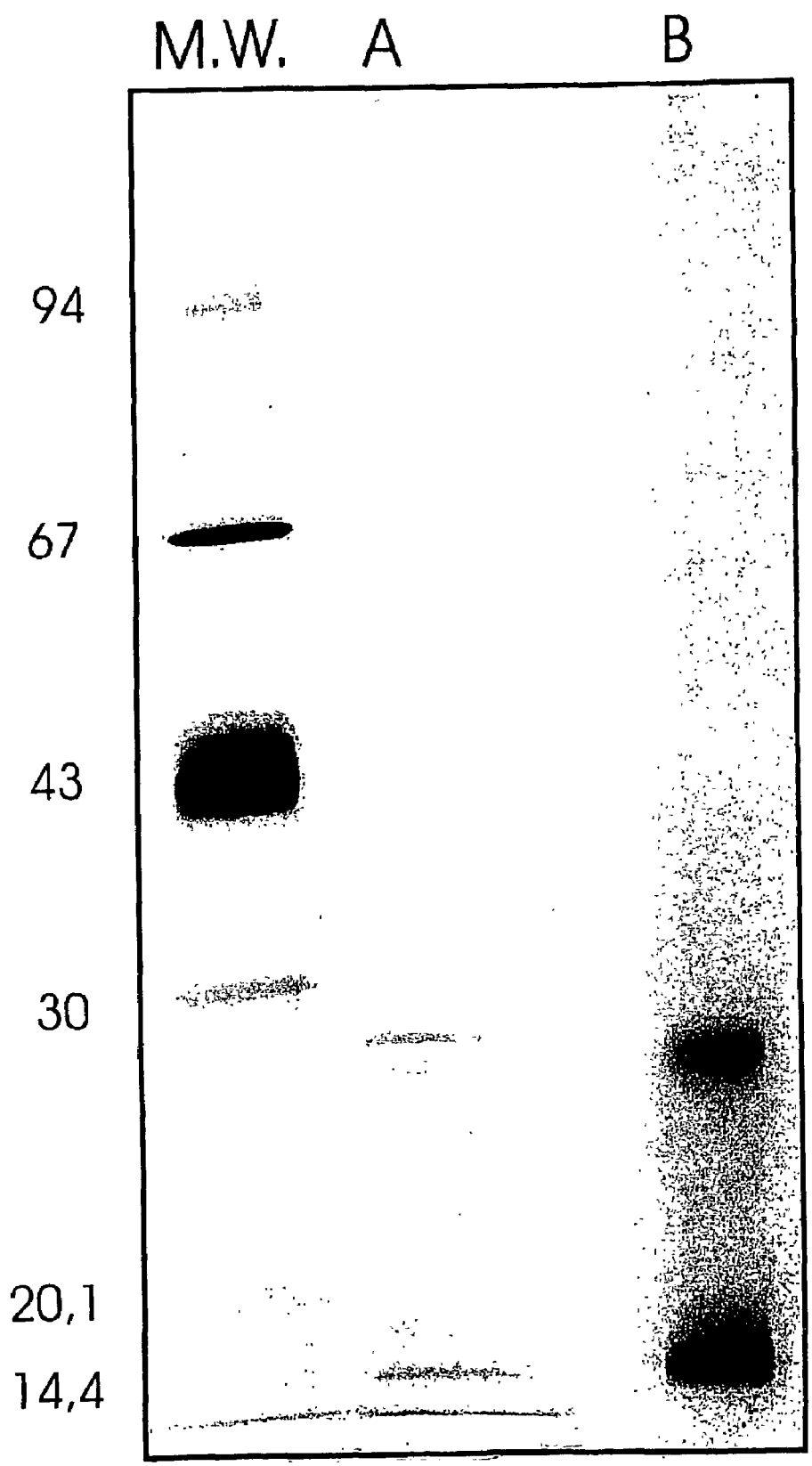
FIG. 12 shows SDS-PAGE of FPLC fraction 40 of SGE derived from *D. reticulatus* adult females run under non-reducing conditions. M.W.=molecular weight markers and track (A) are silver stained SDS-polyacrylamide gels and (B) shows $^{125}$I-IL-8 binding following electroblotting onto a PVDF membrane.

Both bands migrating at approximately 10-18 kD and the band of approximately 25-30 kD show strong binding of $^{125}$I-IL-8 (FIG. 12).

The results shown in FIG. 12 are a further indication that anti-IL-8 activity is due to an SGE molecule(s) that binds IL-8.

Example 8

Inhibition by Tick SGE of IL-8 Binding to the IL-8 Cell Receptor

Ten ml of fresh human blood were collected in a tube with 10 µl of heparin ($5 \times 10^3$ U/l ml; Léciva Praha) and diluted 1:1 in 0.9% NaCl solution. Cell suspension was resuspended in 24 ml of deionised water for 30 sec to lyse erythrocytes, then 8 ml of 3.6% NaCl solution were added and the cells were centrifuged at 1000 rpm (K 23) for 10 min. The cell pellet was washed with 0.9% NaCl solution and centrifuged at 1000 rpm (K 23, Janetzki) for 10 min. Cells were resuspended in 2 ml RPMI supplemented with 10% FCS. Cell number was determined using Türk's solution and diluted to $4 \times 10^6$ and/or $2 \times 10^6$ granulocytes per milliliter.

SGE from *D. reticulatus* adult females fed for 5 days was diluted in 50 µl of PBS at a final concentration 50 µg and/or 10 µg and/or 5 µg. Ten µl of each fraction were diluted in 40 µl of PBS. IL-8 was used in the assay at a final concentration 50 ng in 50 µl of either PBS or solution of SGE. 1.2 µl of $^{125}$I-IL-8 was diluted in 50 µl of either PBS or solution of either SGE or fraction.

For the radioassay, mixtures of $^{125}$I-IL-8 with either SGE or FPLC fraction or PBS (control) were incubated for 1 hour at room temperature. The mixtures were then added to cells (200,000 per well) and incubated for 1 hour at room temp. Cell suspensions were 3 times washed with PBS. Pellets of cells were resuspended in 50 µl PBS and measured using a gammacounter. To demonstrate specific binding (competition of radiolabelled and unlabelled IL-8), cells were pretreated for 30 min with unlabelled IL-8.

Figure 13:
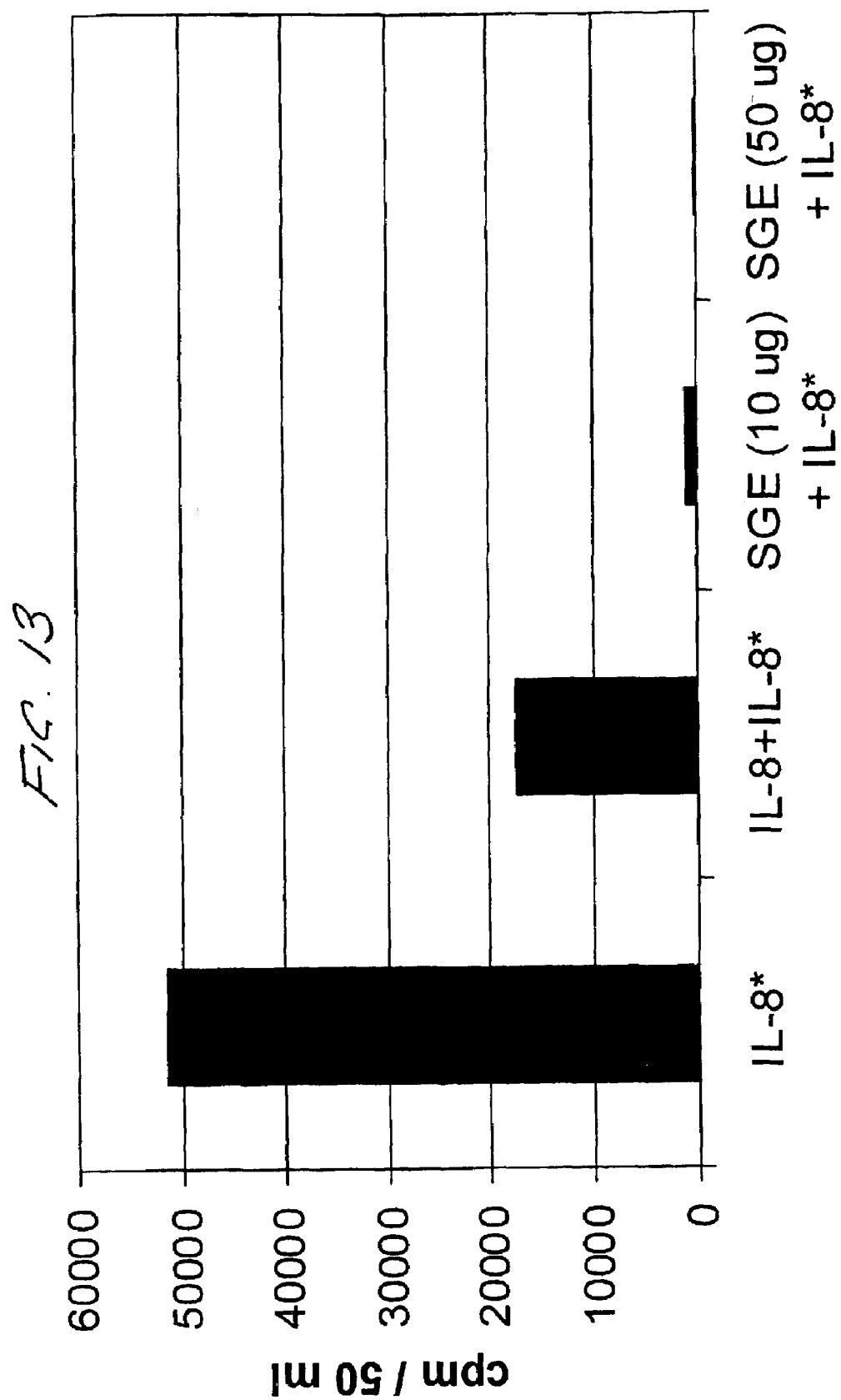
FIG. 13 shows the inhibition by tick SGE of $^{125}$I-IL-8 binding to its cell receptor. IL-8*=$^{125}$I-IL-8 binding to its receptor; IL-8+$^{125}$I-IL-8=radiolabelled IL-8 bound to its receptor in the presence of cold (unlabelled) IL-8; SGE (10 μg)+$^{125}$I-IL-8=radiolabelled IL-8 bound to its receptor when treated with 10 μg of tick SGE; SGE (50 μg)+$^{125}$I-IL-8 radiolabelled IL-8 bound to its receptor when treated with 50 μg of tick SGE. SGE was from *D. reticulatus* adult females fed for 5 days.
Figure 14:
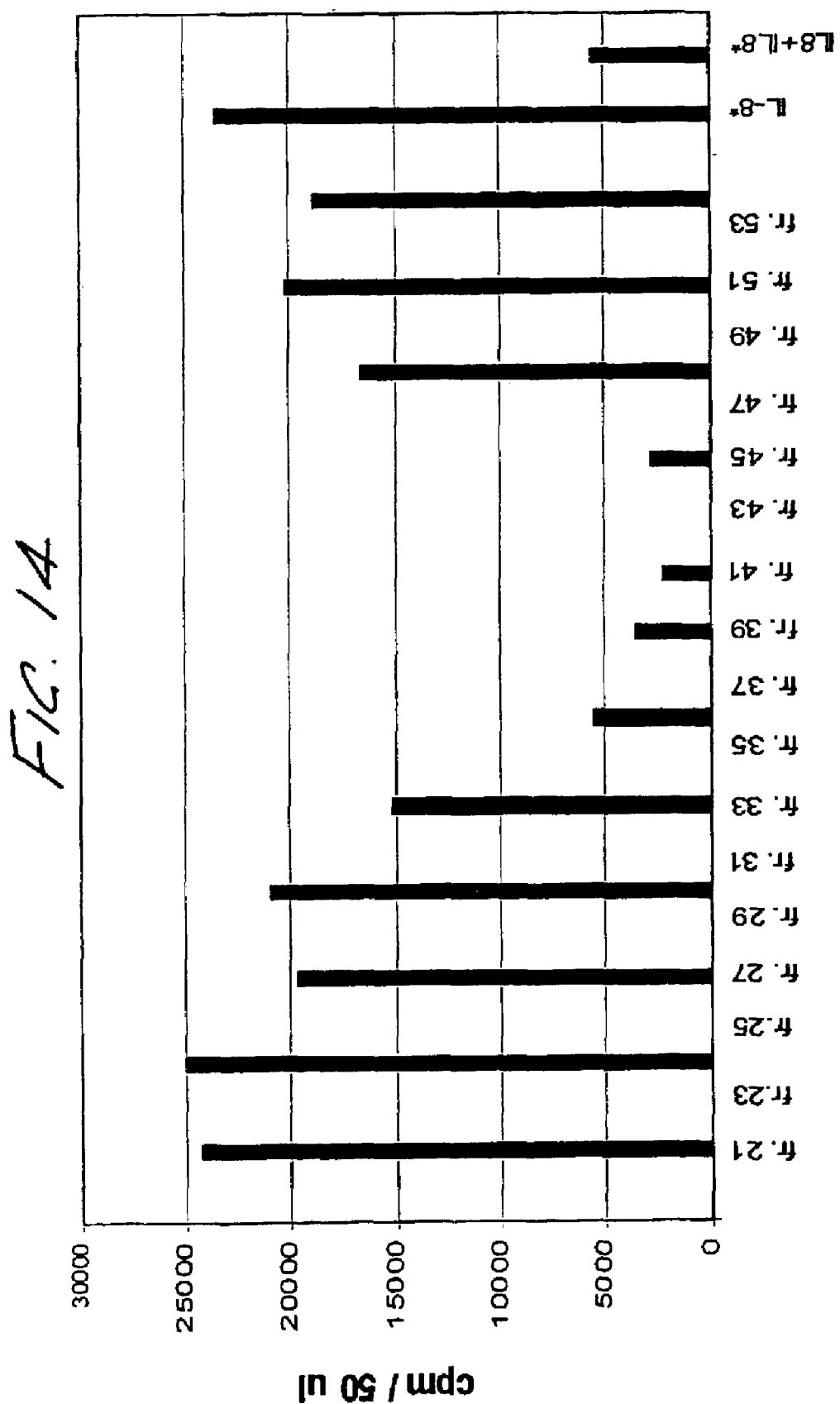
FIG. 14 shows the inhibition $^{125}$I-IL-8 binding to its cell receptor by FPLC fractions of tick SGE. IL-8*=$^{125}$I-IL-8 binding to its receptor; IL-8+$^{125}$I-IL-8=radiolabelled IL-8 bound to its receptor in the presence of cold (unlabelled) IL-8; fr.xx=radiolabelled IL-8 bound to its receptor when treated with fraction as numbered. SGE is from *D. reticulatus* adult females fed for 5 days.

FIG. 13 shows the inhibition by tick SGE of $^{125}$I-IL-8 binding to its cell receptor. When the cells were pretreated with cold (unlabelled) IL-8, the amount of $^{125}$I-IL-8 binding to its receptor was reduced, indicating the specificity of receptor binding. When $^{125}$I-IL8 was treated with either 10 µg or 50 µg SGE, there was a substantial dose dependent reduction in binding of the radiolabelled IL-8 to its receptor, indicating that anti-IL-8 activity is due a molecule(s) in SGE that binds to IL-8 and thereby prevents IL-8 binding to its receptor. When the assay was repeated using FPLC fractions of SGE from *D. reticulatus* adult females fed for 5 days, peak inhibition of IL-8 binding to its receptor occurred when IL-8 was treated with fractions 36 to 45 (FIG. 14). The results are in accordance with those obtained using ELISA (Example 3).

Example 9

Inhibition by Tick SGE of IL-8 Chemotactic Activity

Agarose plates were prepared according to the method of van Damme and Cunings (1995). Solution A comprised 2 ml foetal calf serum (FCS, Biocom), 2 ml 10× concentrated Eagle's minimum essential medium (EMEM, Sigma) with Earle's salts, L-glutamine and sodium-bicarbonate, and 6 ml distilled water. The medium was pre-warmed to 50° C. Solution B comprised 0.18 g agarose (Indubiose, IBF) boiled in 10 ml distilled water until completely dissolved and cooled to 50° C. Solutions A and B were then mixed in equal volumes and poured into 3 plastic tissue culture dishes (6 ml per 1 dish Ø 6 cm) and were allowed to cool. The dishes were transferred to a refrigerator (4° C.) until further processing. Immediately before the chemotaxis assay, a series of six rows (per dish) of three wells were made using a punch and vacuum.

Granulocytes were isolated from human peripheral blood using a modification of the method described by van Damme and Cunings (1995). Briefly, 10 to 15 ml fresh human blood were collected in a tube with heparin and diluted 1:1 in 0.9% NaCl solution. The cell suspension was carefully loaded onto a 10 ml mixture of Ficol–Telebrix (d=1.077–1.079) and centrifuged at 1300 rpm (K 80) for 50 min. The second layer consisting of erythrocytes and granulocytes was washed 3 times with 0.9% NaCl solution and centrifuged at 1000 rpm for 10 min. The cell pellet was resuspended in 24 ml of deionised water for 30 sec to lyse the erythrocytes, and then 8 ml of 3.6% NaCl solution was added and the cells were centrifuged at 1000 rpm for 10 min. The cell pellet was washed with 0.9 % NaCl solution and centrifuged at 1000 rpm for 10 min. Cells were resuspended in 1 ml EMEM supplemented with 5% FCS. Cell number was determined using Türk's solution and diluted to $3 \times 10^7$ granulocytes per milliliter.

Ten µl IL-8 ($3 \times 10^4$ U/10 µl kindly supplied by Prof. Arden, Belgium) were mixed with either 10 µl SGE (45 µtotal protein), or 10 µl of each test FPLC fraction. The controls were 10 µl IL-8 mixed with 10 µl or either antibody (2 mg/1 ml) or phosphate-buffered saline (PBS). All the samples were incubated for 30 min at 37° C. in a humidified $CO_2$ (5%) incubator.

For the chemotaxis assay, 10 µl of non-chemotactic medium (negative control) were added to the outer well of each series of three wells. 10 µl of either diluted test sample or standard were added to the inner well. Formylmethionyl-leucylphenylalanine (fMLP) at $10^{-6}$ M was used as a positive control. The centre well of each series of three wells was filled with 10 µl of cells, e.g. $3 \times 10^5$ granulocytes. Agarose plates were incubated for 2 hr at 37° C. in a humidified $CO_2$ (5%) incubator. The assay was terminated by adding absolute methanol (3 ml per dish) to the agarose plates for 30 min at room temperature. The methanol was carefully decanted and the cells were fixed with formaldehyde (3 ml per dish) for 30 min. The agarose was carefully removed from the culture dish and the cells were stained with May-Grünwald's solution (5 ml per dish) for 10 min and Giemsa's solution (5 ml per dish) for 20 min.

Figure 15:
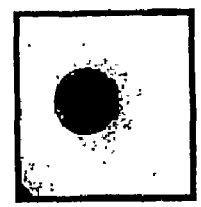
FIG. 15 shows inhibition by tick SGE of the chemotactic activity of IL-8. NC=untreated cells (negative control); fMLP $10^{-6}$=formylmethionyl-leucylphenylalanine at $10^{-6}$ M (positive control of chemotaxis); IL-8 50,000 U=demonstration of chemotactic activity of IL-8; L-8+anti-IL-8=inhibition of chemotactic activity of IL-8 with specific antibodies; IL-8+SGD D.R.=IL-8 treated with *D. reticulatus* SGE; IL-8+fr. 35=IL-8 treated with FPLC fraction 35 of *D. reticulatus* SGE; IL-8+fr. 39=IL-8 treated with FPLC fraction 39 of *D. reticulatus* SGE; IL-8+fr. 50-52=IL-8 treated with FPLC fractions 50 to 52 of *D. reticulatus* SGE.
Figure 15:
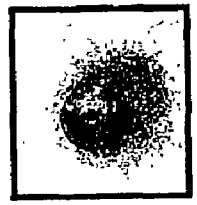
Figure 15:
Figure 15:
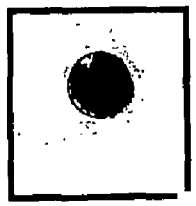
Figure 15:
Figure 15:
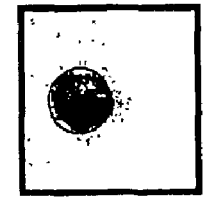
Figure 15:
Figure 15:
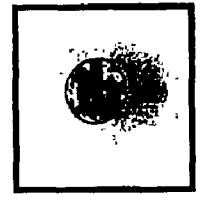

The results (FIG. 15) show that the chemotactic action of IL-8 was inhibited when IL-8 was treated with either anti-IL-8 antibodies (control), or with SGE derived from *D. reticulatus* adult females fed for 5 days or FPLC fraction 35 or 39. By contrast, IL-6 chemotactic activity was unaffected by the treatment of IL-8 with a mixture of FPLC fractions 50-52. These results show that the anti-IL-8 activity of SGE detected in the preceding examples was able to inhibit the biological activity (i.e. chemotaxis) of IL-8.

Furthermore, these results confirm the potential of a technique using SGE to isolate a bioactive compound (IL-8) from a liquid containing this cytokine, in the same way that anti-IL-8 antibodies allow such separation.

Example 10

Figure 16:
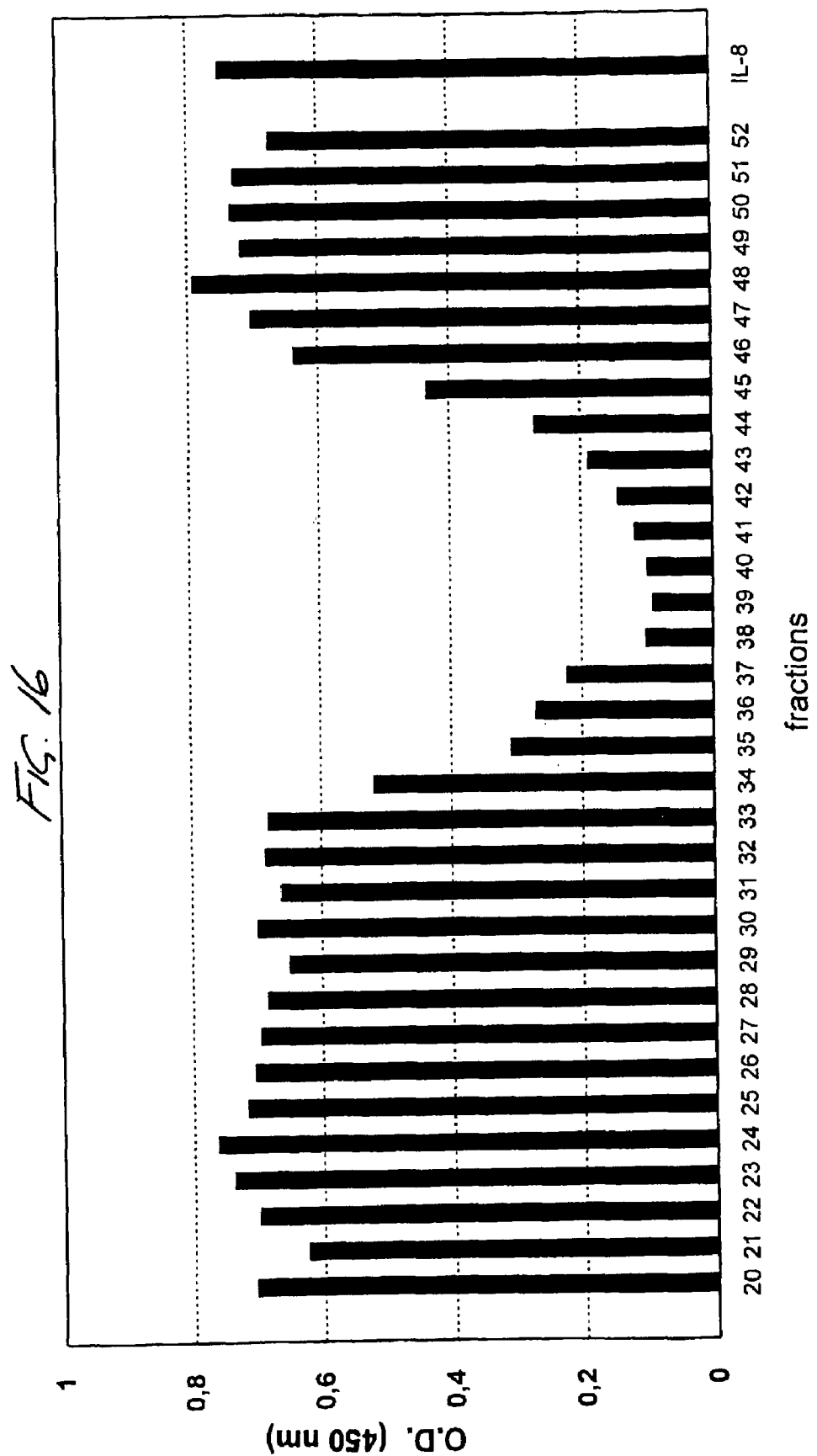
FIGS. 16 and 17 compare the anti-IL-8 and anti-MIP-1α activities of the same FPLC fractions of tick SGE. Fractions were incubated with either 100 pg IL-8 (FIG. 16) or 85 pg MIP-1α (FIG. 17) and then screened by ELISA specific for either chemokine. SGE was derived from *D. reticulatus* adult females fed for 5 days.
Figure 17:
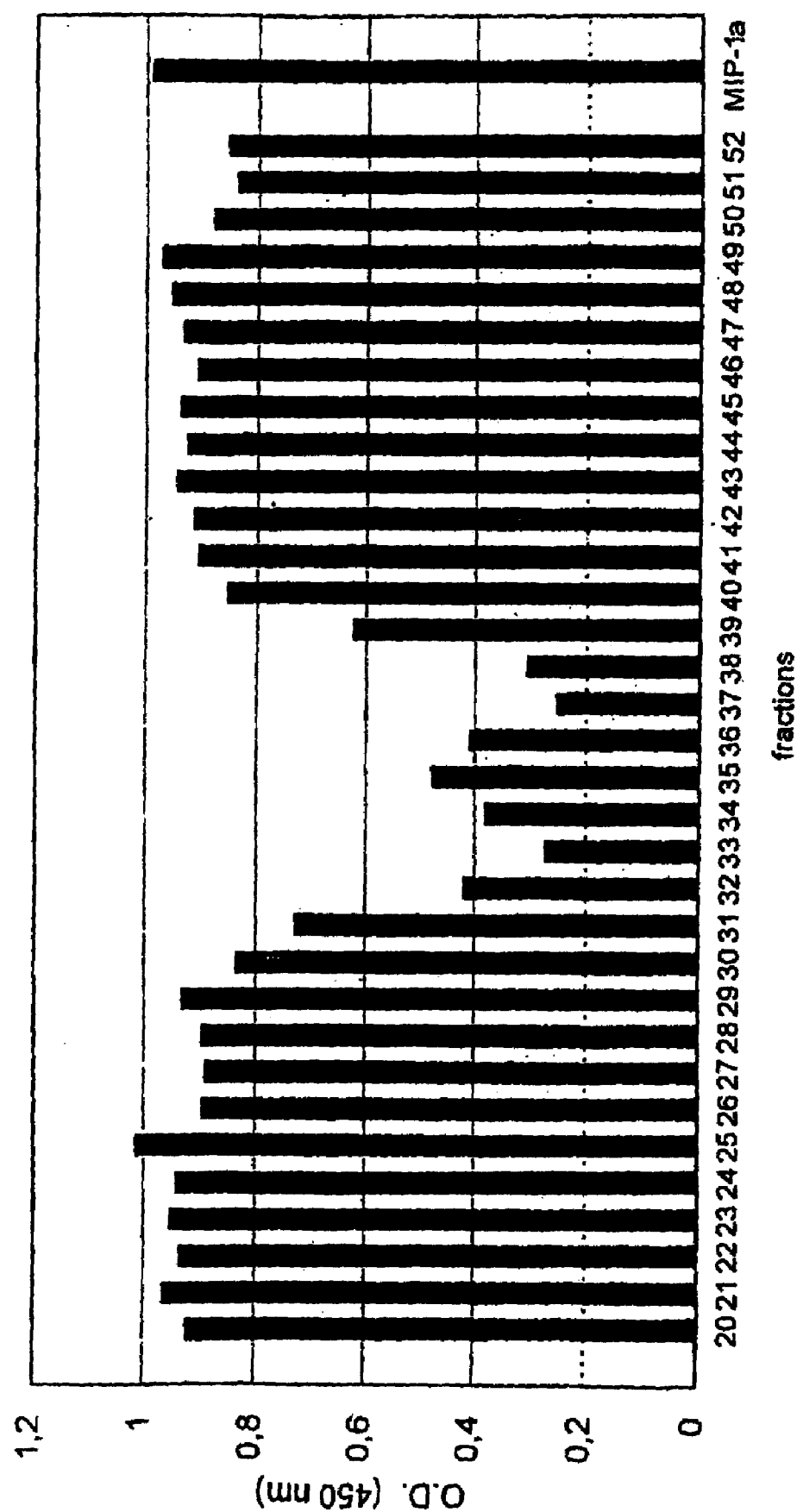

Comparison of Anti-IL-8 and Anti-MIP-1α Activity in FPLC Fractions of Tick SGE The anti-IL-8 activity of FPLC fractions of 4.1 mg SGE (derived from 174 adult female *D. reticulatus* fed for 5 days) was compared with anti-MIP-1α activity (using MIP-1 Quantikine human MIP-1α Immunoassay, R&D Systems Inc., Cat. No. DMA00). All procedures for the MIP-1α assay were similar those used for IL-8. The fractions giving peaks of activity differed indicating that different SGE molecules are responsible for anti-IL-8 (FIG. 16) and anti-MIP-1α (FIG. 17) activities.

Example 11

Effect of FPLC Fractions of *A. variegatum* and *R. appendiculatus* Tick SGE on the Levels of IL-8, MIP-1α, MCP-1 and RANTES The anti-chemokine activity of FPLC fractions of SGE (derived from *A. variegatum* and *R. appendiculatus* ticks) was compared, using the methods described above and in the "Materials and methods" section.

Figure 18:
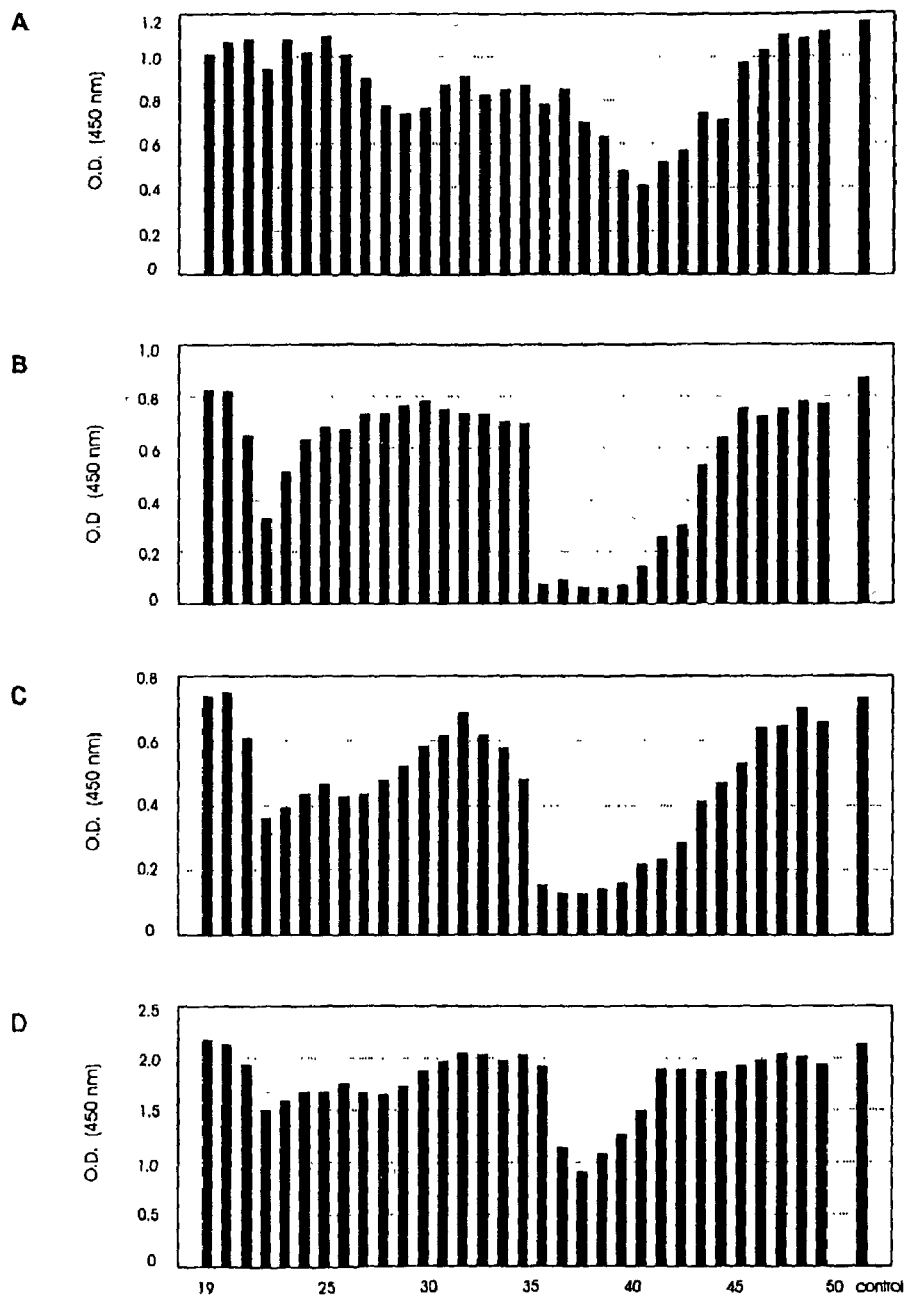
FIG. 18 shows the anti-chemokine activity of FPLC fractions (400 μl) of SGE derived from 11-12 days fed *Amblyomma vareigatum* male ticks (65 ticks, 2.39 mg proteins) ELISA.

In *A. variegatum*, fractions were identified that showed anti-chemokine activity against all of the chemokines IL-8, MIP-1α, MCP-1 and RANTES. These activities are shown in FIG. 18. Compared with activity profiles for *D. reticulatus* SGE fractions (FIG. 4), *A. variegatum* SGE fractions appear to have greater potency against MIP-1α, MCP-1 and RANTES, but less relative potency against IL-8. Comparison of the positions of the different activity peaks suggest that *A. variegatum* SGE contains at least 4 different anti-chemokine molecules. Projects to purify these molecules are presently being conducted.

Figure 19:
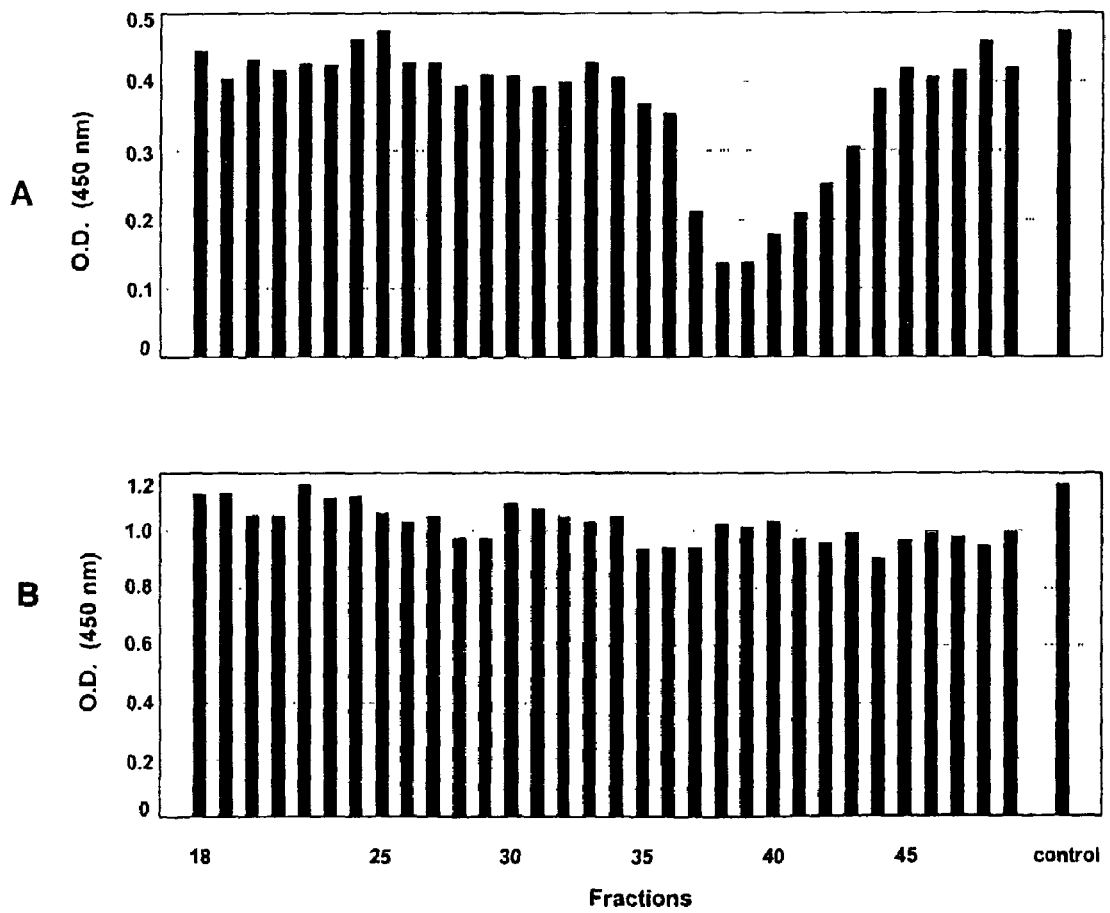
FIG. 19 shows the anti-chemokine activity of FPLC fractions (400 μl) of SGE derived from 5 days fed *Rhipicephalus appendiculatus* female ticks (121 ticks, 1.966 mg proteins) ELISA.

In *R. appendiculatus*, SGE was found to affect IL-8 activity, but not MIP-1α activity. This result is shown in FIG. 19. This is an important result, since it demonstrates that the molecules responsible for anti-chemokine activity may have specific effects on specific types of chemokines. The peak IL-8 activity coincided with that observed for *D. reticulatus* SGE fractions (FIG. 4) and *A. variegatum* SGE fractions (FIG. 18) indicating that different ixodid tick species contain evolutionary variants of the same anti-IL-8 molecule.

REFERENCES

Ausubel E. A. et al Current Protocols in Molecular Biology, Wiley Interscience, New York.

Bradford, M. M. (1976). A rapid and sensitive method for the quantitation of microgram quantities of protein utilizing the principle of protein-dye binding. *Analytical Biochemistry* 72:248-254.

Hajnicka et al (2000) Inhibition of the antiviral action of interferon by tick salivary gland extract. *J. Imm.* In press.

Jones, L. D. et al. (1988). The rearing and maintenance of ixodid and argasid ticks in the laboratory. *Animal Technol.* 39:99-106.

Kubeš, M., N. et al (1994) Salivary gland extracts of partially fed *Dermacentor reticulatus* ticks decrease natural killer cell activity in vitro. *Immunol.* 84:113-116.

Laemmli, U. K. (1979) Cleavage of structural proteins during the assembly of the head of bacteriophage T4. *Nature* 227:680-685.

Sambrook J. et al (1989) Molecular cloning: a laboratory manual New York: Cold Spring Harbour Laboratory Press.

Van Damme, J. & Cunings, R. (1995) Assay for Chemotaxis. In: Cytokines, a Practical Approach Series, Ed. F. R. Balkwill, Chapter 13: 215-224

The invention claimed is:

1. A method for identifying a receptor or ligand with a biological function in a mammalian host organism, said method comprising the steps of:
   (a) providing a sample of biological material of a mammalian host organism that is suspected of containing the receptor or ligand, wherein said biological material is a heterogenous protein preparation of a biological fluid, wherein said biological fluid is blood, lymph or cerebrospinal fluid, or a protein expression library, wherein said protein expression library is a wound site library, a lambda wound site expression library or a phage display library;
   (b) bringing said sample of biological material from a mammalian host organism that is suspected of containing the receptor or ligand into contact with a preparation of saliva or salivary glands of a tick, wherein said preparation comprises a plurality of proteins and peptides and said plurality of proteins and peptides is immobilized to a support or tagged to aid in isolation of complexes formed by tick salivary gland proteins or peptides and mammalian receptors or ligands; and
   (c) isolating from the heterogenous protein preparation, one or more mammalian receptors or ligands that bind to a parasite salivary protein or peptide of the preparation.

2. A method according to claim 1, wherein said sample of mammalian host biological material is isolated from blood.

3. A method according to claim 1, wherein said sample of mammalian host biological material comprises one or more proteins isolated from the host organism.

4. A method according to claim 3, wherein said one or more proteins isolated from the host organism are produced by recombinant means.

5. A method according to claim 4, wherein said one or more recombinant proteins are generated by expression from a host gene cloned under the control of a heterologous promoter.

6. A method according to claim 5, wherein said one or more recombinant proteins are the products of a gene expression library.

7. A method according to claim 1, wherein said preparation of saliva is a preparation of salivary extract.

8. A method according to claim 7, wherein said preparation of salivary extract is a fraction of a salivary extract.

9. A method according to claim 1, wherein said sample of mammalian host biological material is brought into contact with an expression library derived from the salivary gland of at least one tick species.

10. A method according to claim 1, wherein said method includes a step of affinity purification, antigen panning, plasmon resonance detection, or comprises a competitive binding assay or yeast two hybrid system.

11. A method according to claim 10 wherein either said preparation of the saliva or salivary glands of a tick or the biological material from the mammalian host organism is tagged to aid the isolation of the host receptor or ligand bound to said parasite salivary compound.

12. A method according to claim 11 wherein said preparation of the saliva or salivary glands of a tick is bound to a support.

13. The method according to claim 12 wherein said support is a resin.

14. A method for identifying a receptor or ligand with a biological function in a mammalian host organism, said method comprising the steps of:

(a) providing a sample of biological material of a mammalian host organism that is suspected of containing the receptor or ligand, wherein said biological material is a heterogenous protein preparation of a biological fluid, wherein said biological fluid is blood, lymph or cerebrospinal fluid, or a protein expression library, wherein said protein expression library is a wound site library, a lambda wound site expression library or a phage display library;

(b) bringing said sample of biological material from a mammalian host organism that is suspected of containing the receptor or ligand into contact with a preparation of saliva or salivary glands of at least one tick species, wherein said preparation comprises a plurality of proteins and peptides and said plurality of proteins and peptides is immobilized to a support or tagged to aid in isolation of complexes formed by tick salivary gland proteins or peptides and mammalian receptors or ligands; and (c) isolating from the heterogenous protein preparation, one or more mammalian receptors or ligands that bind to a parasite salivary protein or peptide of the preparation.

* * * * *